US006435043B1

(12) United States Patent
Ferguson et al.

(10) Patent No.: US 6,435,043 B1
(45) Date of Patent: Aug. 20, 2002

(54) IMPACTION SUBSTRATE AND METHODS OF USE

(75) Inventors: Stephen T. Ferguson, N. Billerica; Ilias G. Kavouras, Boston; Jack M. Wolfson, Jamaica Plain; Petros Koutrakis, Wellesley, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/540,397

(22) Filed: Mar. 31, 2000

Related U.S. Application Data
(60) Provisional application No. 60/127,470, filed on Mar. 31, 1999.

(51) Int. Cl.$^7$ .............................................. G01N 15/10
(52) U.S. Cl. ................................... 73/863.22; 73/865.5
(58) Field of Search .......................... 73/863.22, 865.5; 55/462; 95/32

(56) References Cited

U.S. PATENT DOCUMENTS

| | | | | |
|---|---|---|---|---|
| 3,957,017 A | * | 5/1976 | Carmignani et al. | 119/3 |
| 4,133,202 A | * | 1/1979 | Marple | 73/28 |
| 4,176,165 A | * | 11/1979 | Hargett et al. | 423/245 |
| 4,251,238 A | * | 2/1981 | Claes et al. | 55/97 |
| 4,321,822 A | * | 3/1982 | Marple et al. | 73/28 |
| 4,725,294 A | * | 2/1988 | Berger | 55/270 |
| 4,796,475 A | | 1/1989 | Marpel | |
| 4,926,679 A | | 5/1990 | Dewhurst | |
| 4,961,966 A | | 10/1990 | Stevens et al. | 427/299 |
| 5,183,481 A | * | 2/1993 | Felder | 55/15 |
| 5,302,191 A | * | 4/1994 | Koutrakis et al. | 95/285 |
| 5,437,198 A | | 8/1995 | John | |
| 5,553,795 A | | 9/1996 | Tsai et al. | |
| 5,693,895 A | * | 12/1997 | Baxter | 73/863.22 |
| 5,904,752 A | * | 5/1999 | Willeke | 95/216 |
| 5,983,732 A | * | 11/1999 | Hering et al. | 73/863.22 |

FOREIGN PATENT DOCUMENTS

| | | | |
|---|---|---|---|
| CH | CH 597 895 A | 4/1978 | |
| WO | WO 98 32001 A | 7/1998 | |
| WO | WO 00/58708 | * 3/2000 | ............ G01N/1/24 |

OTHER PUBLICATIONS

Pierce, R.C. et al. "Dependency of Polynuclear Aromatic Hydrocarbon Content on Size Distribution of Atmospheric Aerosols." *Environ. Sci. Technol.*, 9, 347–353 (1975).

Milford, J.B. et al. "The sizes of particulate trace elements in the atmosphere—a review." *J. Air. Poll. Control. Assoc.*, 35, 1249–1260 (1985).

Venkataraman, C. et al. "Size distributions of polycyclic aromatic hydrocarbons and elemental carbon. 1. Sampling, measurement methods, and source characterization." *Environ. Sci. Technol.*, 28, 555–562 (1994).

Marple, V.A. et al. "Characteristics of Laminar Jet Impactors." *Environ. Sci. Technol.*, 8, 648–654 (1974).

Chen, B.T. et al. "Performance of a Modified Virtual Impactor." *Aerosol. Sci. Technol.*, 5, 369–376 (1986).

Marple, V.A. et al. "A Microorifice Uniform Deposit Impactor (MOUDI): Description, Calibration, and Use." *Aerosol. Sci. Technol.*, 14, 434–446 (1991).

Fang, C.P. et al. "Influence of cross–flow on particle collection characteristics of mutli–nozzle impactors." *J. Aerosol. Sci.* 22, 403–415 (1991).

Sehmel, G.A. "Particle Suspension: A Review." *Environ. Intern.*, 4, 107–127 (1980).

(List continued on next page.)

*Primary Examiner*—Hezron Williams
*Assistant Examiner*—C D. Garber
(74) *Attorney, Agent, or Firm*—Dana M. Gordon; Foley Hoag LLP

(57) ABSTRACT

The present disclosure relates to a method of collecting particles in a gas sample comprising impacting particles in the gas sample on a porous material, as well as to impactors wherein an inertial impactor includes a porous substrate.

66 Claims, 25 Drawing Sheets

OTHER PUBLICATIONS

Wall, S. et al. "Measurements of Kinetic Energy Loss for Particles Impacting Surfaces." *Aerosol. Sci. Technol.*, 12, 926–946 (1990).

John, W. et al. "Resuspension induced by impacting particles." *J. Aerosol. Sci.*, 22, 723–736 (1991).

John, W. et al. "Breakup of Latex Doublets by Impaction." *Aerosol. Sci. Technol.*, 19, 57–68 (1993).

Reischl, G.P. et al. "The collection efficiency of impaction surfaces: a new impaction surface." *Stuab. Reinhalt. Luft*, 38–55 (1978).

Pak, S.S. et al. "Effect of Coating Thickness on Particle Bounce in Inertial Impactors." *Aerosol. Sci. Technol.*, 16, 141–150 (1992).

Tsai, C.J. et al. "Solid Particle Collection Characteristics on Impaction Surfaces of Different Designs." *Aerosol. Sci. Technol.*, 23, 96–106 (1995).

Biswas, P. et al. "The particle trap impactor." *J. Aerosol. Sci.*, 19, 113–121 (1988).

Lundgren, D.A. "An Aerosol Sampler for Determination of Particle Concentration as a Function of Size and Time." *J. Air Poll. Control Assoc.*, 17, 225–229 (1967).

Vanderpool R.W. et al. "Cocalibration of Four Large–Particle Impactors." *Aerosol. Sci. Technol.*, 7, 177–185 (1987).

Sioutas, C. et al. "Inertial collection of fine particles using a high–volume rectangular geometry conventional impactor." *J. Aerosol. Sci.*, 28, 1015–1028 (1997).

Marple, V.A. et al. "Low flow rate sharp cut impactors for indoor air sampling: design and calibration." *Journal of Air Pollution Control Association*, 37, 1303–1307 (1987).

\* cited by examiner

□ THEORETICAL $d_{50}$
○ EXPERIMENTAL $d_{50}$ (OIL-impregnated porousmetal)
△ EXPERIMENTAL $d_{50}$ (Polyurethane foam, FU $F_3$)

Fig. 21

IMPACTION SUBSTRATE AND METHODS OF USE

RELATED APPLICATIONS

This application claims priority to U.S. Provisional Patent Application serial No. 60/127,470, filed Mar. 31, 1999, the contents of which is incorporated by reference.

BACKGROUND OF THE INVENTION

Atmospheric particles play an important role in atmospheric processes and human health. Indeed, particles can absorb or reflect solar radiation and can act as cloud condensation nuclei (CCN) (Charlson, R. J., Schwartz, S. E., Hales, J. M., Cess, R. D., Coakley, J. A., Hansen, J. E., and Hofinann D. J. *Science,* 255, 423–429 (1992); Novakov, T. and Penner, J. E. *Nature,* 365, 823–826 (1993)). Furthermore, particles can become trapped in different regions of the human respiratory tract and have been implicated in premature death, difficult breathing, aggravated asthma, increased hospital admissions, and increased respiratory problems to children (Seaton, A., MacNee, W., Donaldson, K. and Godden, D., *Lancet,* 345, 176–178 (1995)). Because of these undesirable characteristics, measurement of particle concentrations has become increasingly valuable as a regulatory tool as well as for determining health hazards.

The magnitude of the impact of airborne particles on both atmospheric processes and human health is influenced by the size distribution of these particles. Longer lifetimes and higher optical extinction efficiencies of fine aerosol (aerodynamic diameter $d_p < 2.5$ μm) compared to coarse particles ($2.5 < d_p < 10$ μm) are the main reasons for the direct and indirect effects of airborne particles on climate changes (Seinfeld, J. and Pandis, S., Atmospheric Chemistry and Physics: From Air Pollution to Climate Changes, John Wiley & Sons, London, England (1997)). Moreover, exposures to particles with diameters less than 2.5 μm have special importance, due to the findings of epidemiological and clinical studies, which showed a relationship between ambient particle concentration and increased respiratory problems and mortality rates—(Utell, M and Samet, J., Airborne particles and respiratory disease: Clinical and pathogenetic considerations, in *Particles in our Air,* Wilson R, and Spengler J. D., Eds., Harvard University Press (1996)). Thus, the ability to accurately measure concentrations of particles within specific size ranges is of considerable importance.

Conventional inertial impactors have been used to classify ambient particles according to their diameter (Pierce, R. C. and Katz, M., D, *Environ. Sci. Technol.,* 9, 347–353 (1975); Milford, J. B. and Davidson, C. I., *J Air. Poll. Control. Assoc.,* 35, 1249–1260 (1985); Venkataraman, C., Lyons, J. M. and Friedlander, S. K., *Environ. Sci. Technol.,* 28, 555–562 (1994)). The performance of conventional inertial impactors has been studied extensively, and their behavior and characteristics can be predicted quite accurately (Marple, V. A. and Liu, B. Y. H., *Environ. Sci. Technol.,* 8, 648–654 (1974); Marple, V. A., Rubow, K. L., and Olson, B. A., *Aerosol Measurement,* Willeke, K. and Baron, P. A. Eds., Van Nostrand Reinhold, New York, 106–232 (1993)). The appropriate type of the impaction substrate depends on the species and chemical analysis to be performed.

Other types of samplers have been designed and developed. One such sampler is the virtual inertial impactor. One limitation of virtual impactors is the lack of complete separation of particles for sizes below the cut point, resulting in a mixture of concentrated coarse particles and unconcentrated fine particles in the minor flow of the impactor (Chen, B. T., Yeh, H. C. and Cheng, Y. S., *Areosl. Sci. Technol.,* 5, 369–376 (1986)). A different type of conventional impactor with a rotating stage design, the microorifice uniform deposit impactor, has also been developed, (MOUDI) (Marple, V. A., Rubow, K. L. and Behm, S. M., *Areosl. Sci. Technol.,* 14, 434–446 (1991)). With the MOUDI, it is still possible for bounce-off and re-entrainment losses to occur, since several tens of layers of particles are accumulated during sampling. Furthermore, multiple jet interactions can deteriorate the performance of the impactor, affecting both the cut-off point and internal losses (Fang, C. P., Marple, V. A. and Rubow, K. L. *J. Aerosol.Sci.* 22, 403–415 (1991)).

Many of these types of impactors and substrates used for collection of ambient particles (e.g., solid flat plates and thin porous membranes (generally 0.2 min or thinner)) exhibit decreased particle collection efficiency under such conditions. The decreased particle collection efficiency is a result of at least two factors: particles of high momentum impact the substrate and bounce off, and particles which have been previously collected are displaced from the substrate and re-entrained in the airstream (Sehmel, G. A., *Environ. Intern.,* 4, 107–127 (1980); Wall, S., John, W., Wang, H. C. and Coren, S. L., *Areosl. Sci. Technol.,* 12, 926–946 (1990); John, W., Fritter, D. N. and Winklmayr, W., *J. Aerosol. Sci.,* 22, 723–736 (1991); John, W. and Sethi, V., *Aerosol Sci. Technol.,* 19, 57–68 (1993)). In addition, because these two processes typically depend on particle size, the size distribution of the collected particles can be substantially distorted, which can confound the results of later physicochemical and biological tests performed with the collected particles.

To overcome these problems, porous metallic or glass materials have been used as impaction substrates after having been saturated with mineral oil. However, the collected particles were contaminated by substances present in the mineral oil (Reischl, G. P. and John, W., *Stuab. Reinhalt. Luft,* 38–55 (1978); Pak, S. S., Liu, B. Y. H. and Rubow, K. L., *Aerosol. Sci. Technol.,* 16, 141–150 (1992); Tsai, C. J. and Cheng, Y. H., *Areosl. Sci. Technol.,* 23, 96–106 (1995); Biswas, P. and Flagan, R. C., *J. Aerosol. Sci.,* 19, 113–121 (1988)). The use of oil or grease-coated substrates is an important limitation for collection and analysis of ambient particles in two ways. First, the collection efficiency of these surfaces, as a function of particle size, depends on the amount of particles collected. Thus, the collection efficiency changes during the collection of a sample, as the amount of the material collected increases with time. Second, particles collected on the impactor substrate are contaminated by components of the coating material, prohibiting or interfering with certain types of chemical analysis and toxicological testing.

An impaction substrate capable of more selectively and reliably trapping particles of interest for measurement under a wide range of conditions is critical for ensuring accurate regulation, monitoring, and risk calculation.

SUMMARY OF THE INVENTION

The present invention concerns devices and methods which utilize porous substrates for the collection of particles in a gas sample. The porous substrates are useful as impaction substrates in particle collection devices such as conventional inertial impactor systems. Specifically, the substrates of the present invention can be used to collect particles of a particular size (aerodynamic diameter) range from a gas sample for analysis. They can also be used to remove particles above a given size range to allow for analysis of the particles remaining in the gas sample.

Porous substrates of the present invention offer several advantages over other materials used for the collection of particles. For example, porous substrates are capable of highly efficient particle collection, even under conditions of heavy particle loading. The use of porous materials as impaction substrates also eliminates contamination problems associated with mineral oil-coated substrates, as the porous substrates described herein are uncoated. This characteristic simplifies recovery of particles from the substrate for both chemical analysis and toxicological studies. In addition, the significantly higher collection efficiency and capacity of porous substrates allows for longer sampling time periods without significant distortion of the size distribution of collected particles.

Furthermore, because the porous materials are themselves chemically inert, the collected particles are not contaminated by the substrate and are suitable for physico-chemical and biological testing for effects on respiratory health. In contrast, use of a metal plate may result in contamination by trace metals from the plate itself, and glass fiber filters typically contain substantial amounts of trace elements which can also be a source of contamination.

Another advantage of porous substrates of the present invention is that particles can be collected on a much smaller amount of substrate material, so that it is much easier to recover the collected particles, for characterization and use for toxicological testing.

Thus, in a first aspect, the invention relates to a method of collecting particles in an accelerated gas sample by impacting particles in said gas sample on a porous material. The porous material may include foam, such as polyurethane, or cloth, such as polyester. The porous material may be at least 0.2 mm thick, preferably at least about 1 mm, or even at least about 2 mm thick. The porous material may be substantially free of oil. Additionally, the method may include passing said gas sample through an acceleration nozzle, e.g., a round or slit-shaped nozzle, prior to impacting on said porous material. The method may also include passing said gas sample through a size-selective inlet prior to impacting particles. Additionally, the method may include measuring the quantity or composition of particles deposited on said impacted on said porous material and/or measuring the composition of the airstream which flows past the impaction substrate.

In another embodiment, the invention relates to a method for sampling particles of a particular size range in a gas sample by passing said gas sample through a size-selective inlet to remove particles above a predetermined upper size from said gas sample; passing said gas sample through an acceleration nozzle; and collecting particles which pass through said acceleration nozzle on a porous impaction substrate. The porous impaction substrate may include foam, such as polyurethane, or cloth, such as polyester.

In another aspect, the invention relates to a particle sampler, such as a conventional inertial impactor, having an impaction substrate comprised of a porous material. The porous material may include foam, such as polyurethane, or cloth, such as polyester. The particle sampler may include an acceleration nozzle disposed adjacent to said impaction substrate, and/or a size-selective inlet configured to remove particles above a predetermined size from an airstream before the airstream passes over the impaction substrate.

In another embodiment, the invention provides an inertial impactor having an acceleration nozzle adjacent to an impaction substrate including a porous material as described above disposed adjacent to the acceleration nozzle. The impactor may also include a size-selection inlet configured to remove particles above a predetermined size from an airstream before the airstream passes over the impaction substrate.

In yet another embodiment, the invention relates to an inertial compactor having a sample inlet for receiving a stream of gas, a housing coupled to said sample inlet, an acceleration nozzle mounted within said housing to increase the velocity of the stream of gas, and an impaction substrate comprising a porous material as described above disposed adjacent to said acceleration nozzle to collect particles from said stream of gas. The impactor may further include a size-selective inlet mounted within said housing. Preferably, a size-selective inlet precedes a acceleration nozzle, which in turn precedes the impaction substrate, as an airstream passes through an impactor.

In still another embodiment, the invention provides a multistage gas sampling system comprising a plurality of impaction substrates configured such that a stream of air will pass over the impaction substrates in a series, wherein at least one of said substrates comprises a porous material as described above. The multistage system may include a size-selective inlet, an acceleration nozzle, and/or any other component as described above. Preferably, for each stage of the multistage system, an impaction substrate with an adjacent acceleration nozzle is present.

In yet another aspect, the invention provides a method of manufacturing an inertial impactor by providing a housing, mounting within said housing an acceleration nozzle, and mounting adjacent to said acceleration nozzle an impaction substrate comprising a porous material as described above. The method may additionally include mounting within said housing a size-selective inlet for removing particles above a predetermined size.

Other features and advantages of the invention will be apparent from the following description of the preferred embodiments thereof, and from the claims.

BRIEF DESCRIPTION OF THE FIGURES

FIG. 1 is a schematic diagram of a conventional inertial impactor system with a slit-shaped acceleration jet.

FIG. 2 is a schematic diagram of the test apparatus used for testing the performance of the porous materials used as impaction substrates.

FIG. 3 is a graph showing the losses of generated particles within the test impactor housing and acceleration nozzle for a given particle size. The x-axis represents particle diameter. The y-axis represents % losses.

FIGS. 4A & B are graphs showing the collection efficiency as a function of particle size for $PUF_1$, (density 0.019 g/$cm^3$), using the $PM_8$, size-selective inlet, for two different slit-shaped acceleration jets. FIG. 4A is for slit $S_1$, (0.40[L]×0.37[W]cm). FIG. 4B is for Slit $S_2$(4.50[L]×0.03[W]cm). The x-axis represents particle diameter. The y-axis represents % collection efficiency.

FIGS. 5A–D are graphs showing the collection efficiency as a function of particle size for $PUF_1$, (density 0.019 g/$cm^3$) (5A and 5B) and $PUF_2$ (density 0.031 glcm$^3$) (5C and 5D) using the $PM_8$ size-selective inlet and slit $S_1$, (0.40[L]×0.37[W]cm), for different values of the S/W ratio, for low relative humidity (RH) and for high RH, respectively. The x-axis represents particle diameter. The y-axis represents % collection efficiency.

FIGS. 6A–D are graphs showing the collection efficiency as a function of particle size for $PUF_1$ (6A and 6B) and $PUF_2$ (6C and 6D) using the $PM_2$, size-selective inlet and Slit $S_3(0.57[L] \times 0.03[W]$cm), for different values of the S/W ratio, for low relative humidity (RH) and for high RH, respectively. The x-axis represents particle diameter. The y-axis represents % collection efficiency.

FIG. 7 is a graph showing the collection efficiency as a function of particle size for $PUF_1$, and for various filters using the $PM_8$ size-selective inlet and slit $S_1(0.40[L] \times 0.37[W]$cm). The x-axis represents particle diameter. The y-axis, represents % collection efficiency.

FIG. 8 is a graph showing the collection efficiency as a function of particle size for $PUF_1$, with the $PM_8$ size-selective inlet and slit $S_1(0.40[L] \times 0.37[W]$cm), as a function of sampling time (minutes). The x-axis represents particle diameter. The y-axis represents % collection efficiency.

FIG. 9 is a graph showing the collection efficiency as a function of the particle size and the cut-off point for $PUF_1$ and for oil-coated porous metallic plates used as impaction substrates in Harvard Impactor. The x-axis represents particle diameter. The y-axis represents % collection efficiency.

FIG. 10 presents a schematic diagram of an inertial impactor system.

Figure 13A:
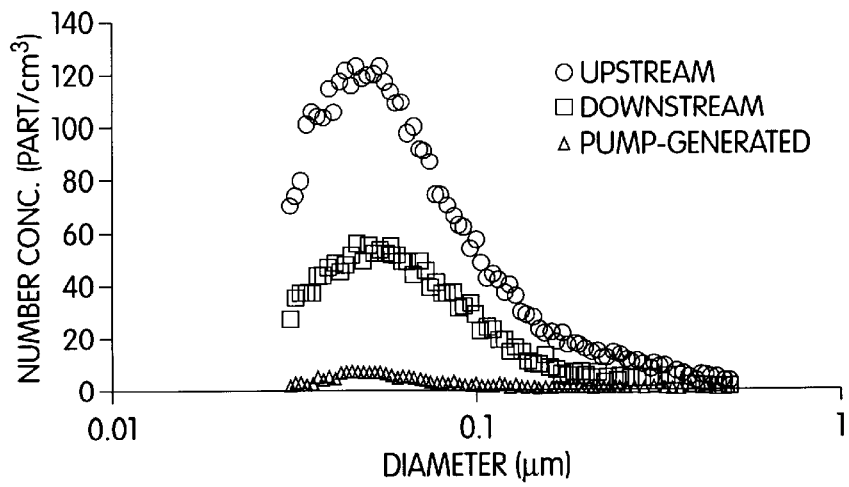
Figure 13B:
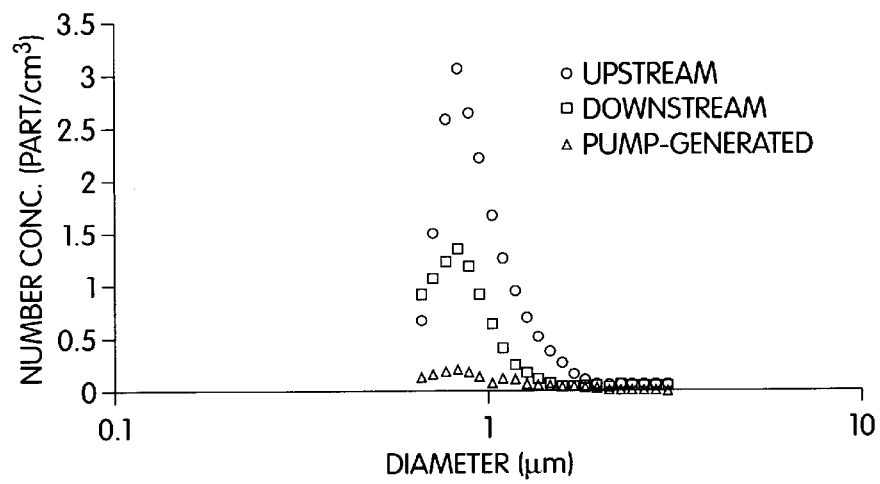
Figure 13C:
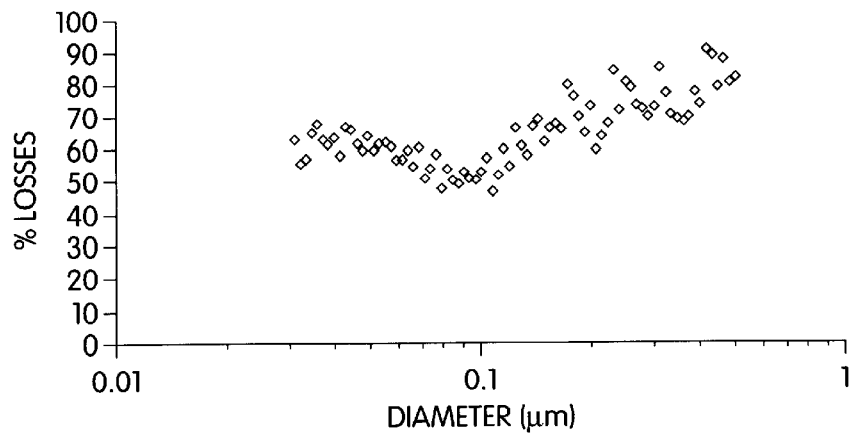

FIGS. 13A–C show particle losses through the secondary pump as a function of size and as a percentage of upstream concentration.

Figure 14:
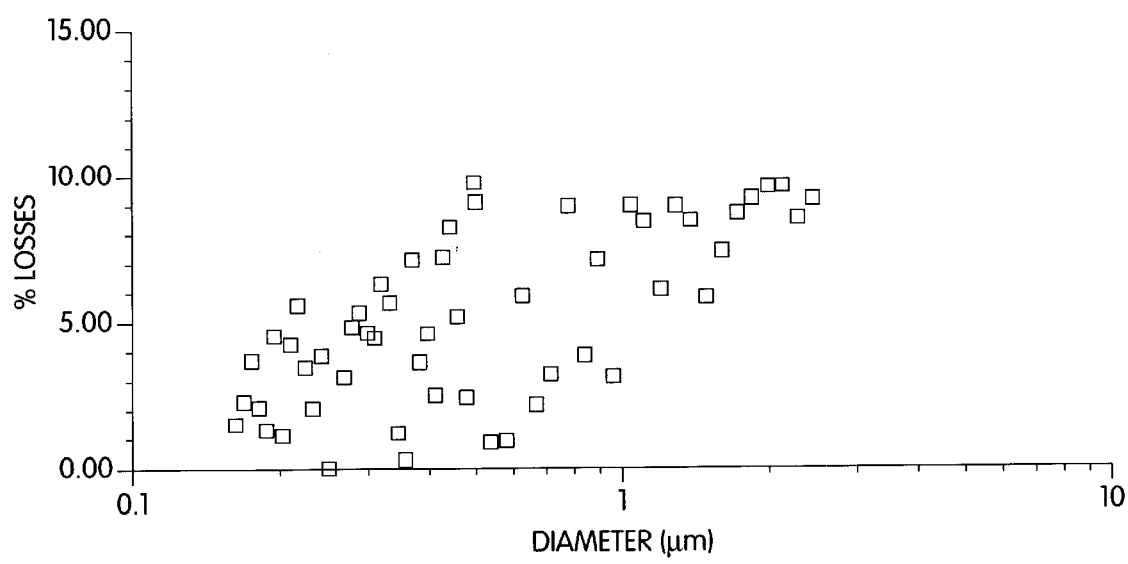

FIG. 14 presents percentage losses through the experimental system as a function of particle size.

Figure 15:
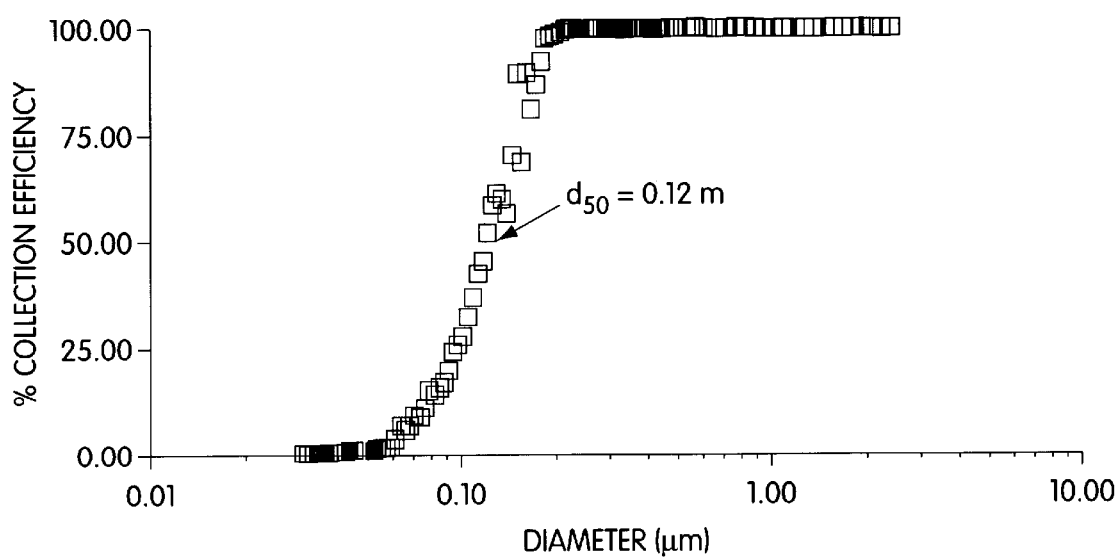

FIG. 15 depicts the collection efficiency of an inertial impactor using a porous impaction substrate as a function of particle size.

FIG

The surface does not function as a filter, as almost all of the gas sample does not pass through the impaction substrate, but rather passes, for example, over, along, or around the impaction substrate. Only particles in the gas sample that acquire sufficient momentum from the acceleration jet strike the impaction substrate. The remaining gas sample, together with particles that do not have enough momentum to impact the substrate surface, passes to the side and/or around the substrate. The impaction substrate absorbs energy from the particle and particles of a desired size range are collected. Without wishing to limit the invention to a particular mechanism, it is believed that particles impinge on the diffuse surface of the porous material substrate and gradually decrease in velocity. The particles then may penetrate into the pores of the substrate, minimizing bounce off and re-entrainment. The greater the velocity of the gas sample through the acceleration jet, the smaller the aerodynamic diameter of the particles that impact on the substrate. Thus, by adjusting the velocity of the gas sample through the acceleration jet, a desired size range of particles can be collected. Preferred materials for use as impaction substrates in the present invention include polymer foams and felt cloths. Such materials can be readily made or are commercially available. For example, polyurethane foams and polyester felt cloth are commercially available (see Table 1, below).

An "inertial impactor" typically refers to a single unit comprising of an air inlet, an acceleration nozzle, and an impaction plate. At the acceleration nozzle exit, the airstreams turns sharply and particles larger than a certain diameter (referred to as the impactor's cut-off size) impinge on the collection surface due to inertial forces. Exemplary inertial impactors are discussed in U.S. Pat. Nos. 5,553,795, 5,437,198, 4,926,679, 4,796,475, 4,321,822, and 4,133,202.

By "multistage" is meant two or more particle collection units, such as inertial impactors, e.g., arranged in a series, such that an airstream passes over two or more particle collection units in succession. Thus, an apparatus may comprise a series of collectors, each selective for particles of a particular size, to sample particles of a wide range of sizes from an airstream, or a series of collectors all selective for particles of the same size, to more efficiently remove particles of that size from an airstream.

By "porous material" is meant a material which has open pores or cells such that a fraction of the volume of the material is open space. Open cells may be interconnected in such a manner that the collected particles can pass from one cell to another. In addition, the porous material of the present invention is preferably not coated with substances, e.g., oil or grease, prior to collection to improve its particle collection efficiency. The porous material preferably has a thickness greater than 0.2 mm, and preferably about 2 mm or larger. Two exemplary materials which have the above-described properties and are particularly useful as porous materials according to the present invention are foams and cloths. Suitable foams include, but are not limited to, those comprising polyurethane, polyethylene, polypropylene and polyester, Suitable cloths include, but are not limited to, those that are woven or nonwoven and which comprise polyester, polyurethane or polypropylene. A preferred cloth is felt cloth. Even more preferred is polyester felt cloth. The porous materials of the present invention can also be composed of metal, graphite/carbon, ceramics and other suitable substances. Those of ordinary skill in the art would be able to identify other materials suitable for use as impaction substrates in the practice of the present invention by choosing materials that comprise open cells, are uncoated, e.g., by grease or oil, and have appropriate thickness, e.g., similar to foam and felt cloths described herein, and comparing the particle collection performance of the chosen materials to that of foam and/or felt cloth.

In certain embodiments, the porous material comprises foam, such as polyurethane polymers. A polyurethane foam preferably has a density between 0.005 g/cm$^3$ and 0.1 g/cm$^3$, more preferably between 0.01 g/cm$^3$ and 0.05 g/cm$^3$, and even more preferably between 0.01 g/cm$^3$ and 0.03 g/cm$^3$. In certain embodiments, the polyurethane foam has a density below 0.05 g/cm$^3$. In certain embodiments, the porous material comprises cloth, such as polyester felt. In certain embodiments, the porous material is part of a conventional inertial impactor, e.g., used in a method which includes passing gas sample particles through an acceleration nozzle prior to impacting on the porous material.

By "series" is meant that multiple stages of a multistage air sampling system are arranged so that the gas sample sequentially passes through each stage of the system.

A "size-selective inlet" removes particles above a certain size (aerodynamic diameter) from a stream or sample of gas. By "remove" is meant that at a predetermined particle size, 50% of the particles are removed from the gas sample and 50% pass through the size selective inlet. For particles of smaller sizes than the predetermined size, most, or almost all, particles pass through the inlet, while for particles of larger sizes, most, or almost all, particles are removed. The substrate of a size-selective inlet is used to collect the particles, which are not necessarily subjected to further analysis. In certain preferred embodiments a size selective inlet comprises an inertial impactor. The size of the particles removed is determined, in part, by the velocity of the gas sample as it comes out of the acceleration nozzle. The higher the velocity, the smaller the size of the particles removed. Thus, by selecting the appropriate acceleration nozzle, a predetermined upper size of particles can be removed from a gas sample. In certain embodiments, a size-selective inlet comprises a filter, an elutriator, or any other device capable of removing particles greater than a predetermined size.

III Exemplification

The invention now being generally described, it will be more readily understood by reference to the following examples which are included merely for purposes of illustration of certain aspects and embodiments of the present invention, and are not intended to limit the invention.

EXAMPLE 1

Polyurethane Foam as a Collection Substrate

Design of a Test Conventional Impactor System

Two different types of polyurethane foam were tested, $PUF_1$, and $PUF_2$, with densities of 0.019 and 0.031 g/cm$^3$, respectively. The single stage conventional inertial impactor used for testing the two types of PUF as impaction substrates is shown schematically in FIG. 1. The impactor has an air inlet (1). The system used three different slit-shaped acceleration jets (2): 1) $S_1$(0.40[L]×0.37[W]cm); 2) $S_2$(4.50[L]×0.03[W]cm); and 3) $S_3$(0.57[L]×0.03[W]cm). Two different size-selective inlets were used, one for $PM_8$ and one for $PM_2$. The flow was 15 LPM for all tests. The impaction substrate (3), located directly below the acceleration jet, was a piece of foam with the following dimensions: for slit $S_1$, 2.50(L) by 1.50(W) by 0.60(H) cm; for slit $S_2$, 6.50 (L) by 0.60 (W) by 0.32 (H); for slit $S_3$, 3.00 (L) by 0.60 (W) by 0.32 (H).

Design of Experimental Test Apparatus

The experimental apparatus is illustrated in FIG. 2. The apparatus includes a nebulizer used to aerosolize polydisperse particles (i.e., having a wide range of sizes) (11), a mixing chamber to dilute and equilibrate the particles at the desired relative humidity (RH) (12), a source of wet or dry filtered (particle-free) air (13), a size-selective inlet (with a cut-off point of either 2 or 8 $\mu$m) (14), a duct (15) as a transition section between the size-selective inlet and sample collection system, which is a conventional slit-nozzle inertial impactor with the polyurethane foam substrate (16), and an Aerodynamic Particle Sizer Spectrometer used to measure particle number concentration as a function of particle aerodynamic diameter (17).

Polydisperse particles were generated by nebulizing an aqueous suspension of 2–20 $\mu$m hollow glass spheres (density, 1.1; Polysciences, Inc, Warrington, Pa.) with a nebulizer (Raabe, O. G., Aerosol Generation, Measurement, and Analysis, Ed. B. Y. H. Liu, Academic Press (1976) page 65), using filtered air at 7 psi. The aerosol was mixed with filtered dry or wet air in order to achieve low (22–28%) and high (78–85%) relative humidities, and then passed through a size selective inlet prior to entering a vertical rectangular duct. The sampler was connected to the bottom of the duct. The size-selective inlet for $PM_8$, with a size cut-off of 8 μm, was used with slits $S_1$ and S2. The size-selective inlet for $PM_2$, with a size cut-off of 2 μm, was used with slit $S_3$. For all tests the flow was 15 LPM (liters per minute). The number concentration and size distribution of particles larger than 0.6 μm was measured using an Aerodynamic Particle Sizer Spectrometer (Model APS 3310, TS1 Inc., St. Paul, Minn.). In each experiment, the concentration and size distribution of particles was measured for 10 minutes without the sampler, 10 minutes with the sampler and 10 minutes without the sampler, and then the same sequence was repeated twice more. In addition, experiments were performed to evaluate losses as a function of particle size due to the impactor housing and acceleration jet, to adequately characterize particle collection efficiency of the impactor substrates.

Losses of generated particles through the accelerating nozzle and within the sampling box are possible due to the change of air streamlines and their high concentration. Therefore, a series of experiments using all three slits $S_1$, $S_2$, and $S_3$, were performed to calculate particle losses. In FIG. 3, the percentage of losses as a function of particle diameter is shown for all slits. The losses in both cases are minimal; they varied from 5% to 15% for particles having diameter between 1 and 2 μm and they were less than 5% for larger particles (2<dp<8).

Method of Determining Particle Collection Efficiency

Although particle losses through the acceleration nozzle and within the impactor housing were relatively low (<15%, see FIG. 3), concentrations measured downstream of the substrate were corrected for these losses. The percent collection efficiency of the PUF substrate, %E, for each size was calculated as follows:

$$\%E=(1-C_{outlet}/C_{inlet})(100)$$

where $C_{inlet}$ is the concentration measured in the duct upstream of the sampler and $C_{outlet}$ is the corrected concentration for a given particle size range after the sampler (with impaction substrate). For $PM_8$, an aerosol particle sizer spectrometer (Model 331OA, TSI, Inc., St. Paul, Minn.) measured the number of particles in each of 57 size ranges from 0.6 to 8 μm, and for $PM_2$ the instrument measured the number of particles in each of 20 size ranges from 0.6 to 2 μm.

Slit Design and Flow Effects

In order to determine the appropriate dimensions for the slit-shaped acceleration jet used for the initial testing of $PUF_1$ as a substrate for conventional inertial impactors, two slit design extremes ($S_1$ and $S_2$) were investigated. The cross-sectional areas of the two were similar, so that the velocity at a flow of 15 LPM would achieve a theoretical size cut-off of 2.5 μm based on using a flat impaction substrate. The first slit, $S_1$, had dimensions 0.40[L]×0.37 [W]cm, with length and width almost identical, while the second slit, $S_2$, had dimensions of 4.50[L]×0.03[W] cm, with a relative high ratio of length to width. For each slit the collection efficiency was measured as a function of particle size for flows between 5 and 15 LPM (5, 7.5, 10, 15). The results of these tests for slits $S_1$, and $S_2$ are shown in FIGS. 4A and 4B, respectively. The objectives of these tests were to determine: 1) which of the two slit designs achieved the highest overall collection efficiency, using the size-selective inlet with a size cut-off at 8 μm ($PM_8$); and 2) what was the optimal flow rate for each of the two slits. It is clear from the results in FIGS. 4A & 4B that slit $S_1$ has the higher overall collection efficiency since it performs better in the size range below 2 μm. For this slit ($S_1$) the flow of 15 LPM yields the highest efficiency. For slit $S_2$ the best overall collection efficiency was found at a flow of 10 LPM.

Collection Efficiency Test Results

FIGS. 5A–D show the collection efficiency as a function of aerodynamic diameter ($d_p$) for $PM_8$ ($d_p$<8 μm), for different values of the S/W ratio with slit $S_1$, for both $PUF_1$ (FIGS. 5A & B), and $PUF_2$ (FIGS. 5C & D), for both low (22–28%) and high (78–85%) relative humidities (RH). The S/W ratio is the ratio of the slit width to the distance between the acceleration nozzle and the impaction substrate. In general, higher collection efficiencies were observed for particles larger than 2 m, indicating that bounce-off losses of these particles are minimal. Overall the efficiencies are higher in high humidity than for low humidity, for both $PUF_1$ and $PUF_2$. Higher collection efficiency for $PM_8$ particles was also observed for both $PUF_1$ and $PUF_2$ with decreasing values of the S/W ratios. For $PM_2$, there is little or no difference in collection efficiency as a function of particle size for S/W ratios of 0.41 and 0.27, for either type of PUF or for different values of RH. However, in all cases, as the S/W ratio is decreased to 0.13 and 0.06, the curves shift to the left (for smaller particle sizes), indicating increases in collection efficiency. Overall, for the smallest particle diameters, there is the most variability in efficiency for both types of PUF, as a function of both S/W ratio and relative humidity.

FIGS. 6A–D show the collection efficiencies for $PM_2$ ($d_p$<2 μm) with slit $S_3$. For $PM_2$, for the smallest diameters, the efficiencies are lowest, as they are for $PM_8$. However, while for $PM_8$, in general, the efficiencies remain high for the larger diameters, for $PM_2$ these efficiencies decrease for the largest diameters. Also, the patterns of efficiency vs. S/W ratio are more complicated, in general, for $PM_2$ compared to those for $PM_8$. Overall, for both $PM_2$ and $PM_8$, there is generally an increase in efficiency as the S/W ratio decreases, but for $PM_2$ the efficiencies for $PUF_2$ are considerably higher for a ratio of 1.15 than for a ratio of 0.7 under low RH, but not high RH. For $PM_2$ with $PUF_1$, the highest efficiencies are for a ratio of 0.7 for both RH ranges. On the contrary, for $PM_8$, the overall efficiencies are considerably higher for $PUF_2$ than for $PUF_1$.

FIG. 7 shows the collection efficiencies for $PM_8$ particles using uncoated and oil-coated $PUF_1$ compared to different types of filters. These include porous (Nuclepore™ (NF); Fluoropore™ (FF), cellulose (CF), and fibrous (quartz, QFF); glass, (GFF)) filters (see Table 1).

TABLE 1

| Impaction Substrate | Characteristics | Manufacturer |
|---|---|---|
| $PUF_1$ | $\rho = 0.019$ g/cm$^3$ | Merryweather Foam, Ohio, USA |
| $PUF_2$ | $\rho = 0.031$ g/cm$^3$ | Adams Foam Rubber Co. Illinois, USA |
| Polyester Felt Cloth | $d = 100$ μm | Le Sac Corp., Indiana, USA |
| Glass Fiber Filter | $d = 0.5$ μm | Anderson, Ohio, USA |
| Quartz Fiber Filter | $d = 0.7$ μm | Anderson, Ohio, USA |
| Cellulose Filter | $d = 8$ μm | Whatman, Waidstone, UK |
| Nuclepore ™ Filter | $d = 2.0$ μm | Corning Separations, ME, USA |
| Fluoropore ™ Filter | $d = 0.5$ μm | Millipore Corp. MA, USA |

ρ: density of PUF
d: nominal pore diameter

These results indicate that collection efficiency for uncoated PUF is higher than all the other substrates for $PM_8$.

Capacity of PUF

Figure 8:
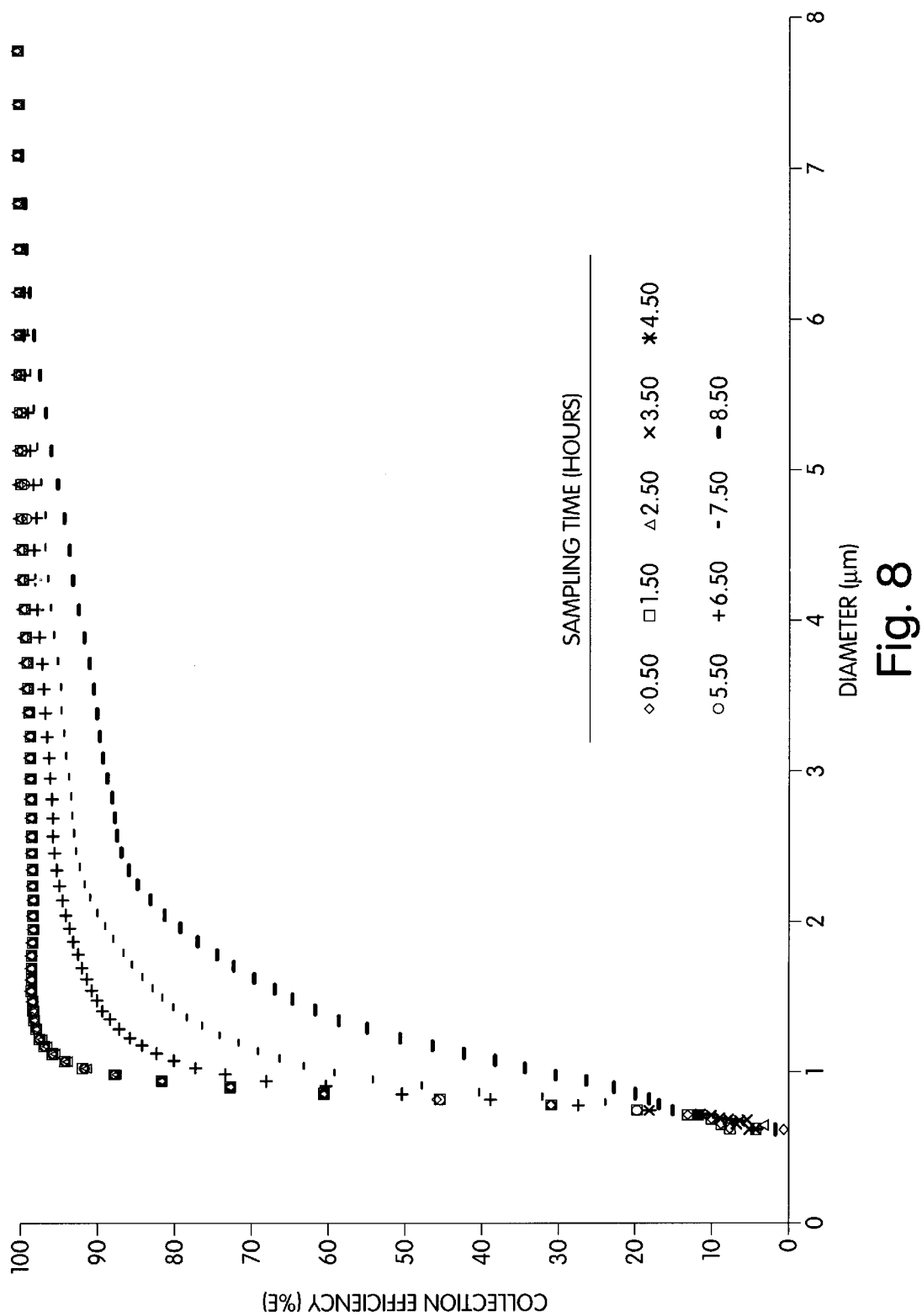

Tests were performed to examine the collection efficiency of $PUF_1$ (using $PM_8$ size-selective inlet and slit $S_1$) for particles as a function of the total amount of particles collected. The results of these tests were used to determine the maximum loading (capacity) below which the high collection efficiency would be maintained (see FIG. 8). The collection efficiency is high and stable for the first 6.75 hours (405 minutes). For longer times, there are decreasing efficiencies of collection for particles having diameter from 1.5 to 2 μm. The mass concentration of generated particles was 5 mg/m$^3$, thus for a flow of 15 LPM, and a sampling period of 6.75 hours, the total collected mass is 30.4 mg. Note that 30.4 mg is the capacity for an impactor using a flow of 15 LPM, with an accelerator slit length of 0.57 cm. A much higher flow of 735 LPM could be used with a longer slit length of about 27.94 cm, with a corresponding capacity of 1.5 g. Typically, a high ambient $PM_{10}$ concentration is about 100 μg/m$^3$ so the sampler could collect ambient particles for a sampling duration of fourteen (14) days. In comparison, other materials used for collection of particles do not allow for efficient collection of anywhere near these amounts of materials.

Comparison of PUF and Mineral-Oil Coated Porous Metal

Many of the currently used particle sampling devices use pre-selective inlets to remove particles above a certain size (for example 10 or 2.5 μm) by impaction. To minimize particle bounce, these methods have used porous metal surfaces that are impregnated with oil or other surfaces coated with grease.

Figure 9:
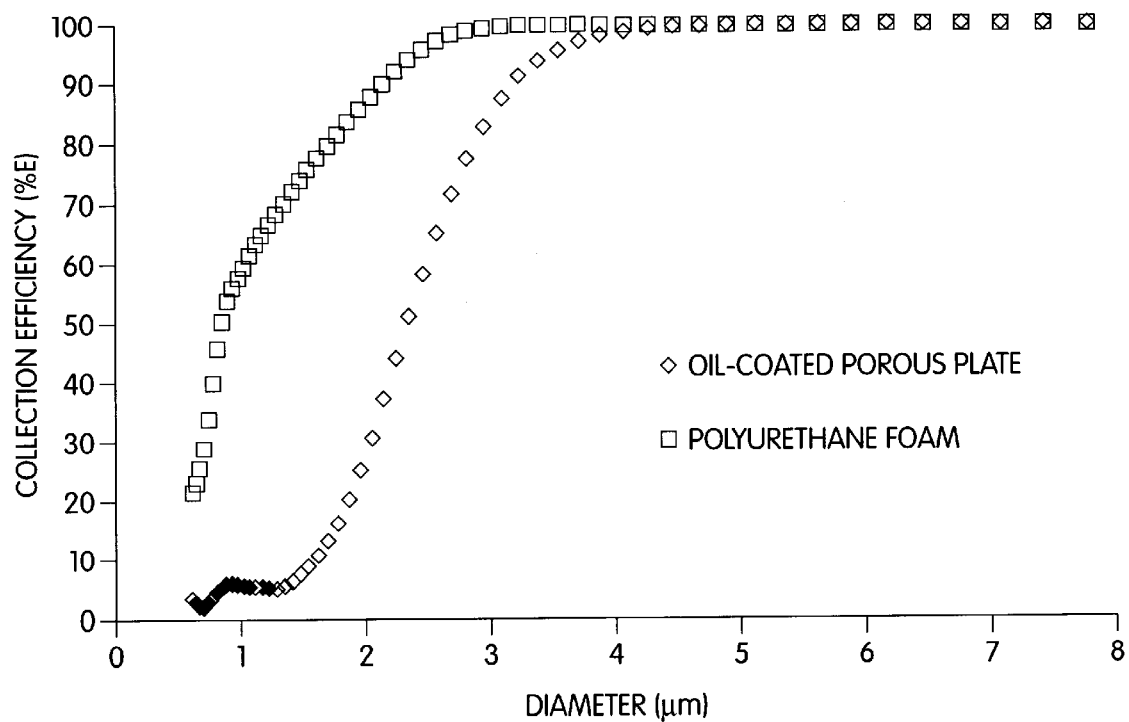

Tests were performed to compare the collection efficiencies of a mineral oil-coated porous metal surface and polyurethane foam substrates using the experimental setup described above. FIG. 9 shows the results of these tests. The collection efficiency of $PUF_1$ is higher than that of the oil-coated surface for the whole range of particle sizes below 4 m. In addition, the use of PUF decreases the 50% cut-point, for the same jet velocity used with the conventional flat surface impactor.

These results suggest that, for the same Stoke's number, the particle size cut-off is lower for porous substrates. This may happen if the properties of the PUF surface cause the effective boundary layer above the surface to be thinner than with previously used substrates.

EXAMPLE 2

Ambient Tests with a Polyester Felt Substrate

For the collection of ambient aerosol a $PM_{2.5}$ size-selective inlet with a $PM_{0.15}$ slit-impactor was used. The dimensions of acceleration nozzles were 5.84[L]×0.03[W] cm. The collection rate was 160 LPM. The dimensions of polyester felt cloth substrate (see Table 1) were 6.60(L)×0.60(W)×0.25(H)cm and the S/W ratio was 0.27. For comparison, sampling was also performed using the Harvard impactor. This impactor has a size-selective inlet with a size cut-off of 2.5 $\mu$m and operates at 10 LPM. Particulate matter was collected by passing the sample air through a Teflon filter placed downstream of the size-selective inlet. Three samples were collected for 24, 48, and 72 hours. The polyester felt cloth substrates were ultrasonically extracted with five (5) ml of ultra-pure $H_2O$ for ninety (90) minutes and Teflon filters were wet with 50 $\mu$l of ethanol and ultrasonically extracted with five (5) ml of ultra-pure $H_2O$ for twenty minutes. The extracted material was analyzed for sulfate anion by ion chromatography. As shown in Table 2, sulfate concentrations measured with Harvard impactor and polyester felt substrates agree within the experimental error (10%). This agreement indicates that the combined collection and extraction efficiency of polyester felt used as an impaction substrate is comparable to that of Teflon filters used to filter the sample air. This confirms that the polyester felt can be used as collection surface for ambient particles and can subsequently be extracted using aqueous solvents. Extraction can also probably be done effectively using organic solvents.

TABLE 2

| Sampling Time | Sulfate Concentration ($\mu$g/m$^3$) | | |
|---|---|---|---|
| (hours) | Harvard Impactor | Polyester Felt | % Efficiency |
| 24 | 1.57 | 1.39 | 88.5 |
| 48 | 2.98 | 2.96 | 99.3 |
| 72 | 2.98 | 2.98 | 99.8 |

EXAMPLE 3

Set-up for Monitoring Ambient Particles for Health Effects

The two size ranges of ambient particles that are important for respiratory health effects are coarse (sizes between 10 and 2.5 $\mu$m) and fine (sizes below 2.5 $\mu$m). To collect particles on porous substrates in each of these sizes separately, size-selective inlets are used upstream of the collecting impactor system. For the coarse particles, the size-selective inlet impactor is a conventional impactor with a size cut-off of 10 $\mu$m. The collecting impactor system for the coarse particles then has a size cut-off of 2.5 $\mu$m, so that the particles collected on the substrate are in the desired size range. For fine particles, the size-selective inlet impactor has a size cut-off of 2.5 $\mu$m, and the collecting impactor has a size cut-off of 0.15 $\mu$m. This size cut-off is small enough to collect on the substrate typically at least 90% of the fine particles from the ambient air sample, since almost all of the ambient fine particles are within the range of 0.15 to 2.5 $\mu$m.

EXAMPLE 4

Multistage Air Sampler

Because the momentum of the particles increases with increasing velocity of the airflow through the jet, it is possible to collect different size categories of airborne particles using different jet velocities. Placing a number of sampling stages with jets of successively increasing velocities in series allows collection of particles segregated by their respective aerodynamic diameters. The principle of this size-segregated collection method has been used previously with other ambient particle collecting samplers (Lundgren, D. A., *J. Air Poll. Control Assoc* 17:225–229 (1967); Vanderpool Lundgren, D. A., Marple, V. A. and Rubow, K. L., *Aerosol. Sci. Technol.*, 7, 177–185 (1987); Marple, V. A., Rubow, K. L. and Behm, S. M., *Aerosol. Sci. Technol.*, 14, 434–446 (1991)). However, the use of porous substrates in a multi-size range impactor system has advantages over previously utilized cascade and multi-orifice (MOUDI) impactor systems. The cascade system uses single round nozzle jet impactors in series, with solid flat plate or thin membrane filter substrates, with a relatively low collection flow (0.3–28 liters per minute (LPM)). It has a relatively high pressure drop across each of the successive impaction stages, and can allow a significant amount of bounce-off and re-entrainment of particles. The MOUDI system also has a relatively low flow (30 LPM), with the same substrates as the cascade system, but has relatively low pressure drops across the successive impaction stages. However, it has a similar potential for bounce-off and re-entrainment as the cascade system. In addition, for the MOUDI system, multiple jet interaction can deteriorate the performance of the impactor, affecting both the cut-point and internal losses, resulting in distortion of the size distribution of the collected particles (Fang, C. P., Marple, V. A. and Rubow, K. L., *J. Aerosol Sci.*, 22, 403–415 (1991)). The advantages of using porous materials as substrates for a size-segregated collection system are the following: 1) slit-shaped jet impactors for each stage can be used which allow for significantly higher collection flows (up to about 1100 LPM); 2) there is negligible bounce-off and re-entrainment, and consequently relatively high collection efficiency; 3) there are relatively low pressure drops across successive impaction stages, which allow for minimal vaporization of semi-volatile components of the collected particles; 4) there is negligible distortion of the size distribution of collected particles; and 5) there is negligible contamination of the collected particles by substances present in the substrate.

A typical multistage air sampler has the following components: 1) a size-selective inlet to remove all particles above a chosen size (such as 10 $\mu$m); 2) a series of conventional impactor stages, with successively smaller size cut-offs (e.g., 5, 2, 0.5, 0.15 $\mu$m), with porous substrate used for each impactor stage: 3) a filter to collect particles smaller than the size cut-off of the last impactor stage, and 4) a vacuum pump to draw sample air through the air sampler components. All of the stages, including the size-selective inlet, are connected in series, so that the sample air, passes through the stages one at a time. Then, for this example, the first impaction stage would collect particles between 10 and 5 $\mu$m, the second impaction stage would collect particles between 5 and 2 $\mu$m, the third impaction stage would collect particles between 2 and 0.15 $\mu$m. Particles<0.15 $\mu$m would be collected on the filter after the fourth stage.

Those of ordinary skill in the art would be able to set up such a multistage air sampler utilizing the porous substrates of the present invention by substituting the porous substrates for those previously used in a multistage air sampler, such as a cascade impactor (Lundgren, D. A., *J. Air Poll. Control Assoc.* 17:225–229 (1967)). Those of skill in the art would also readily appreciate that the porous substrates of the present invention could be used as impaction substrates in other systems with different acceleration nozzles, sizes, types, etc.

EXAMPLE 5

High-Volume Low Cut-Off Impactor

Design and Description of the High Volume Low Cut-off Inertial Impactor (HVLI)

Figure 1:
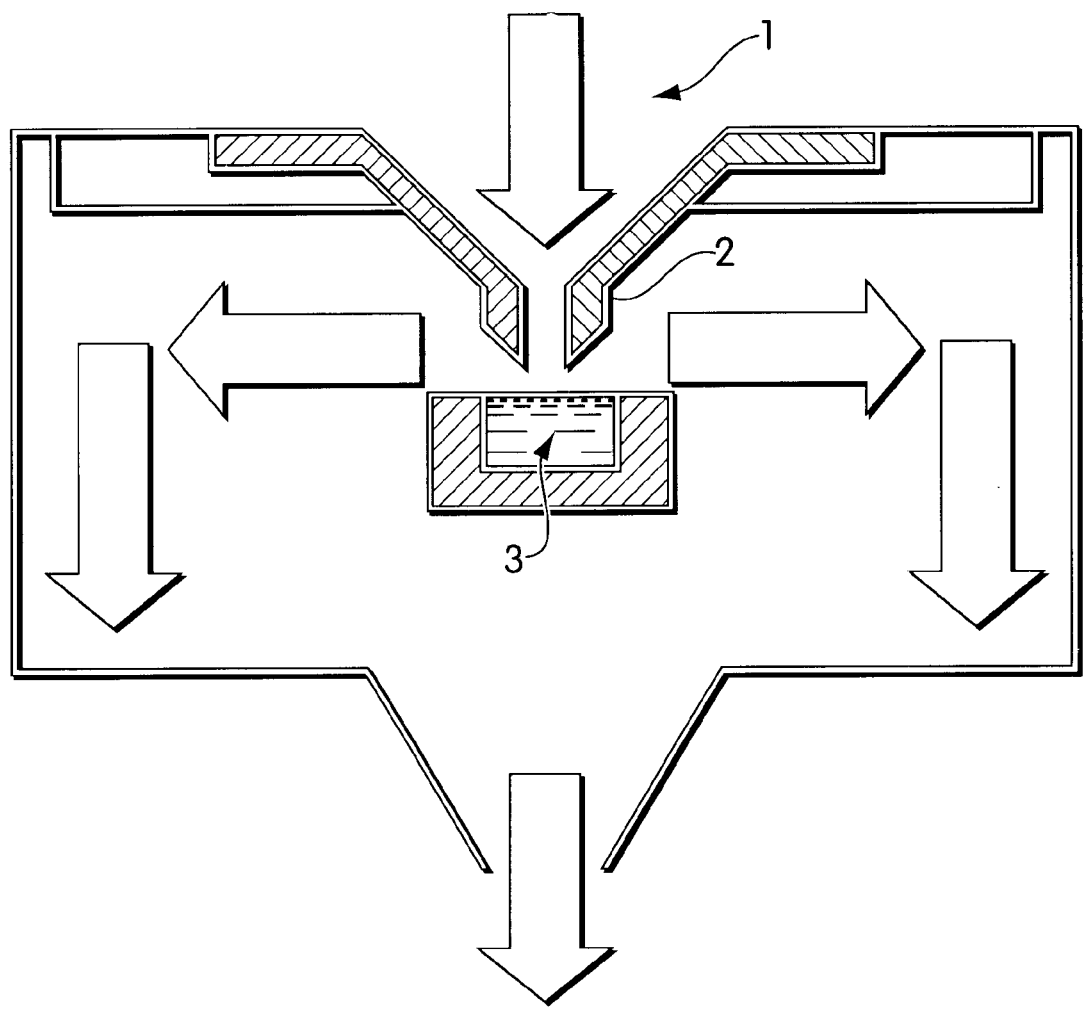
Figure 2:
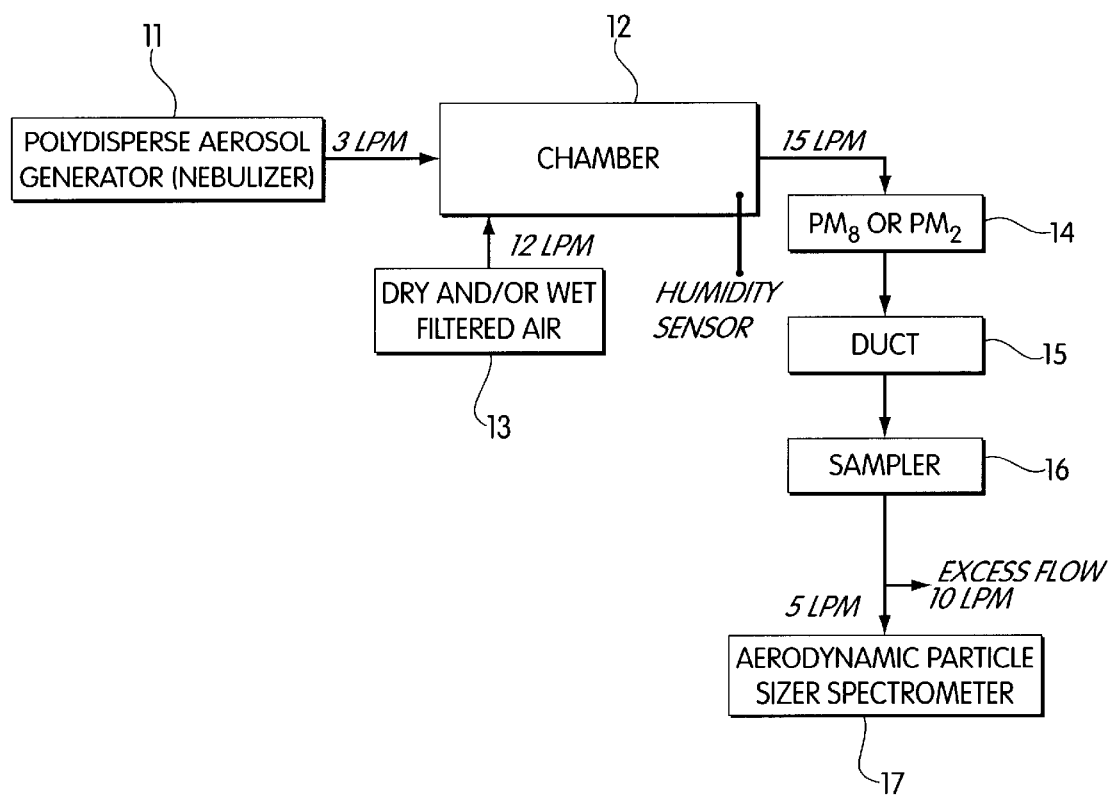
Figure 3:
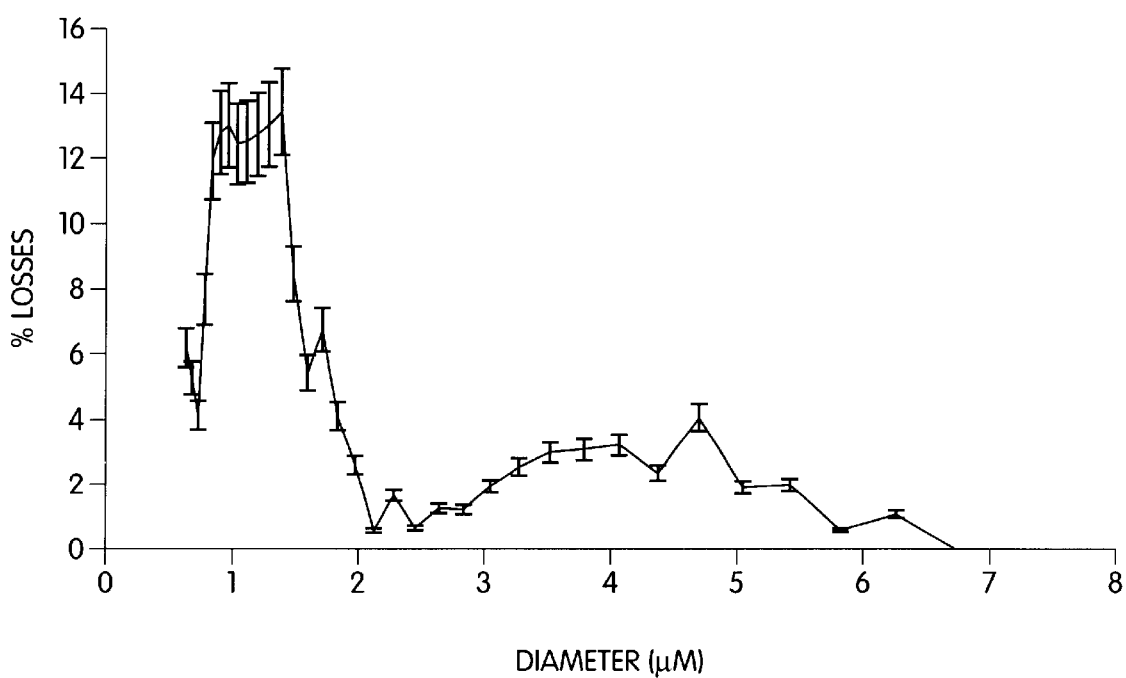
Figure 4A:
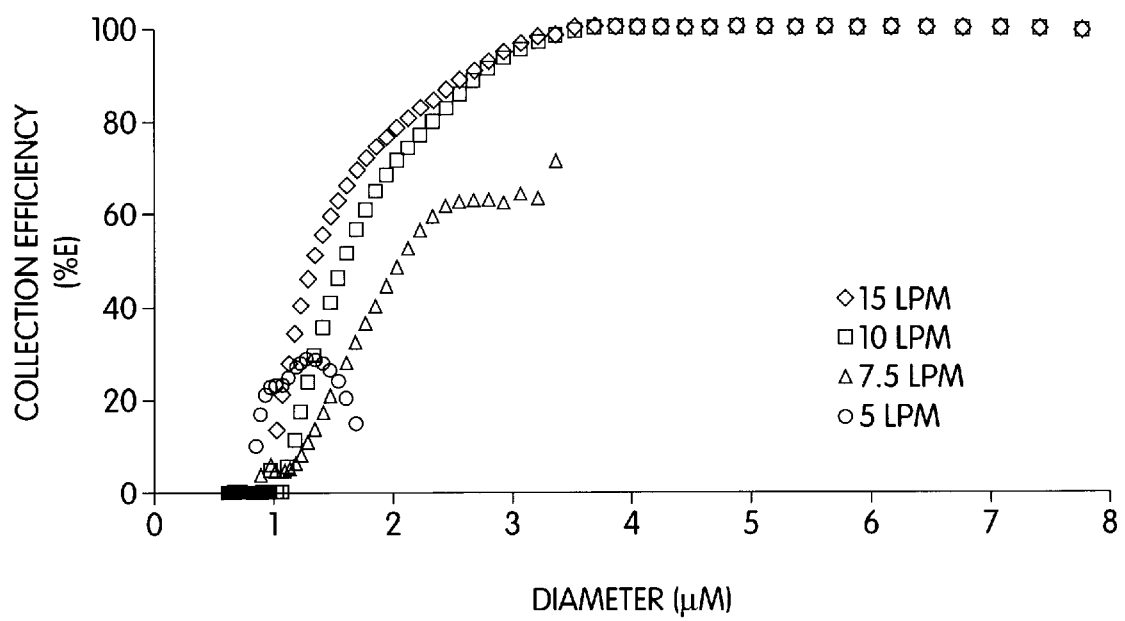
Figure 4B:
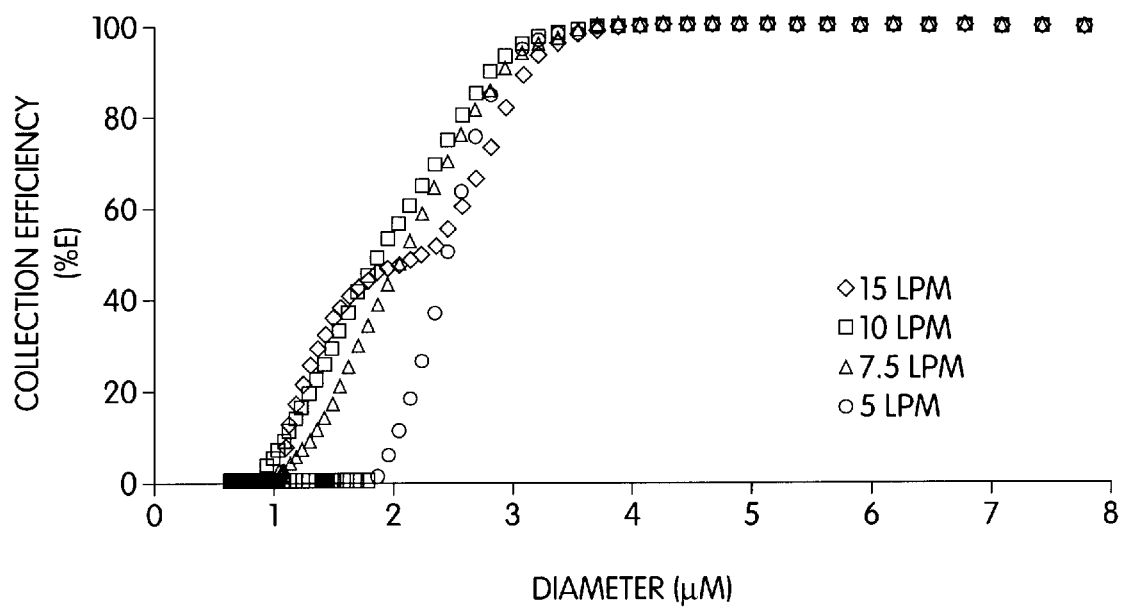
Figure 5A:
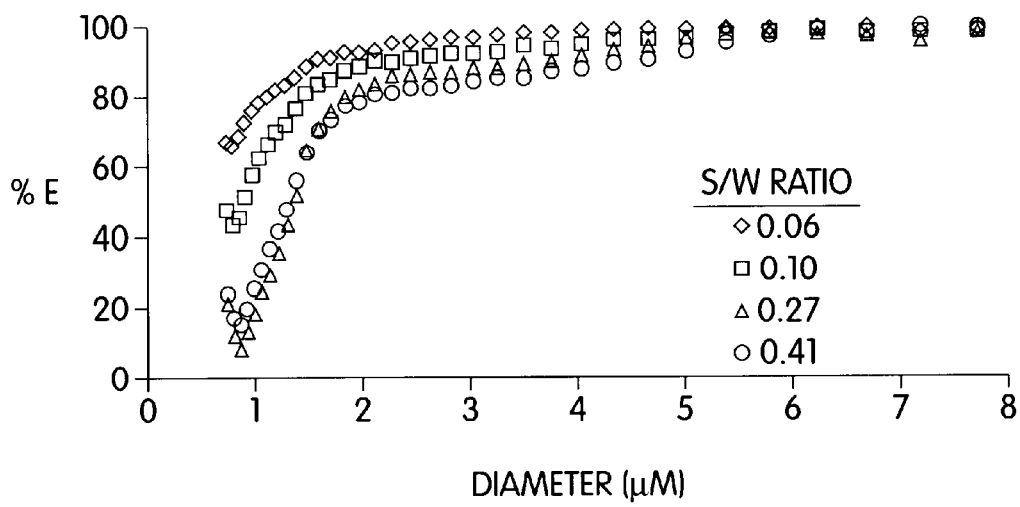
Figure 5B:
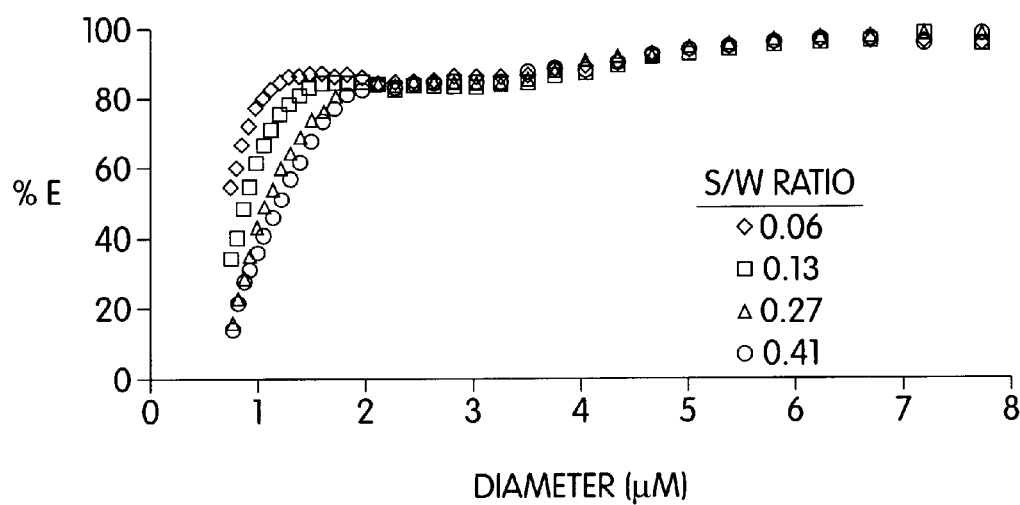
Figure 5C:
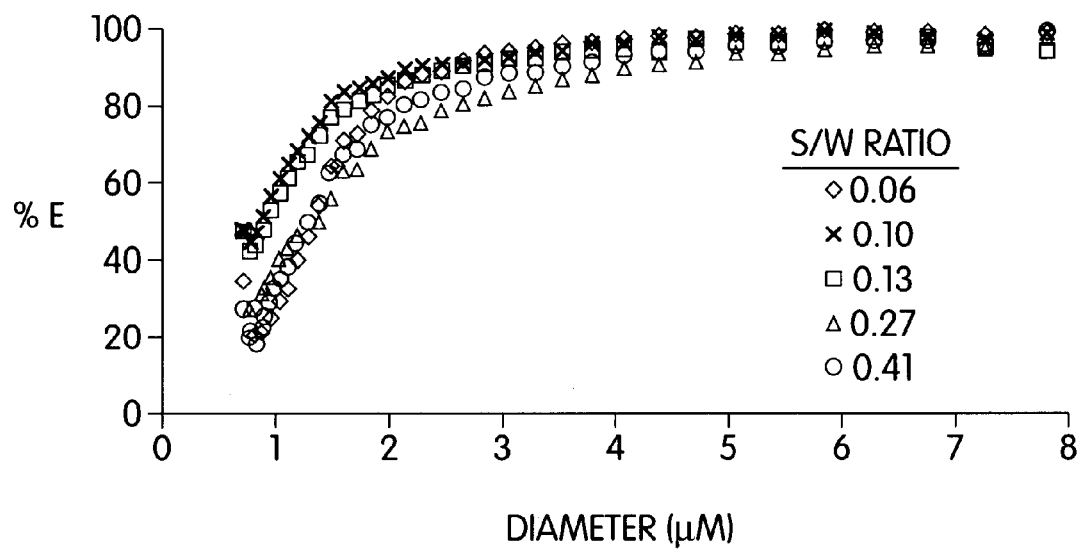
Figure 5D:
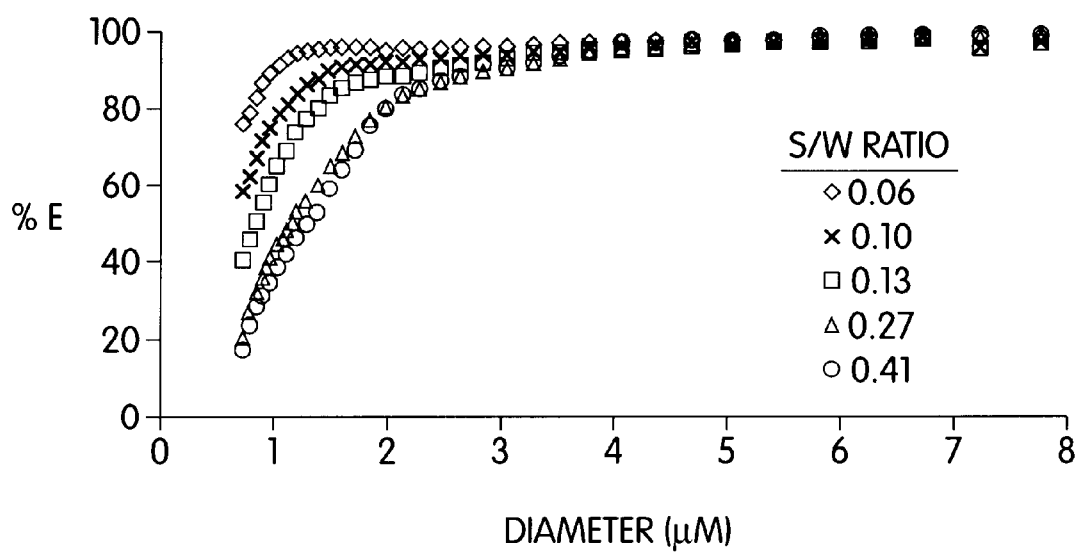
Figure 6A:
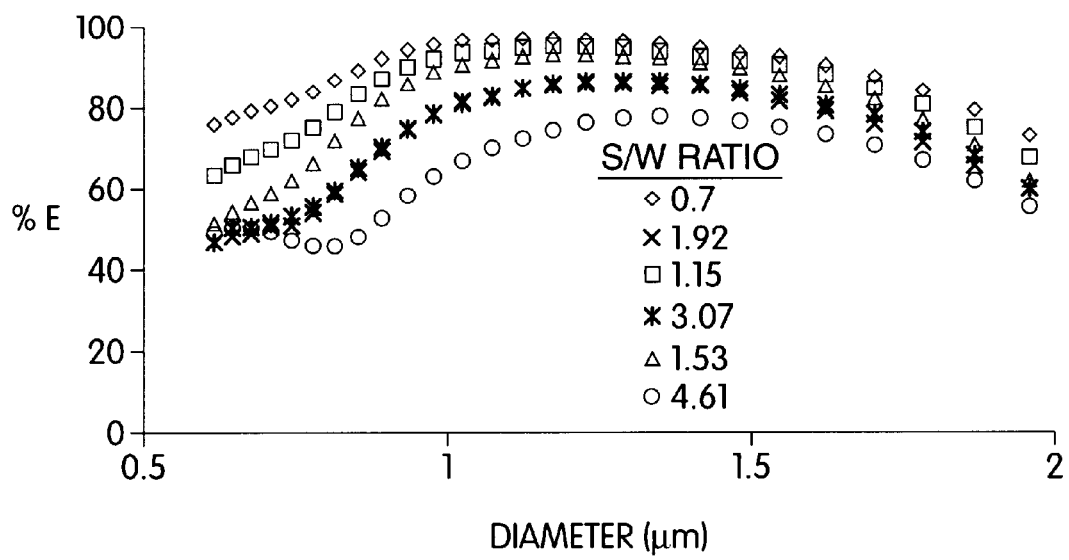
Figure 6B:
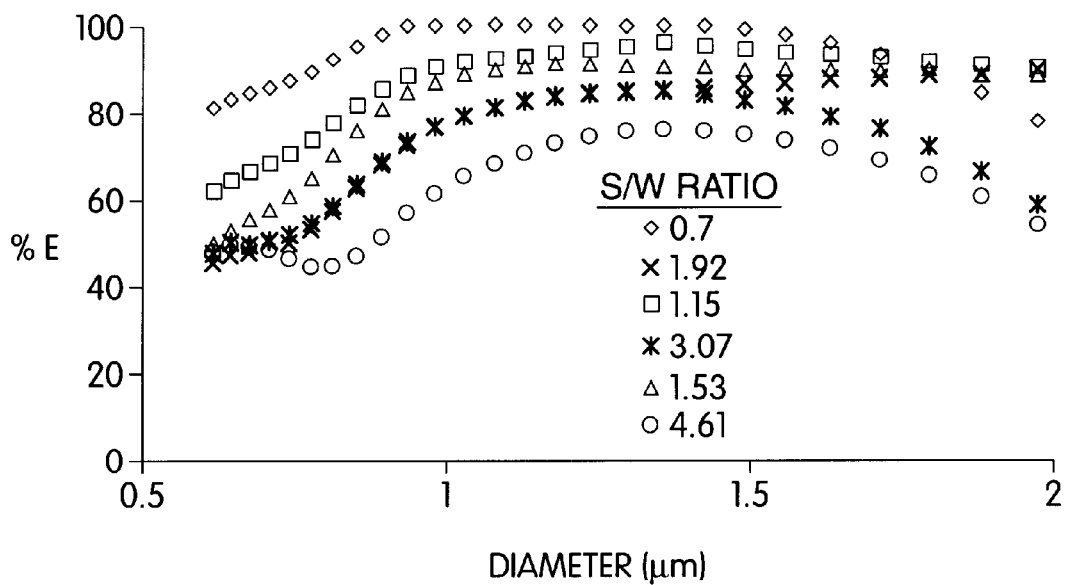
Figure 6C:
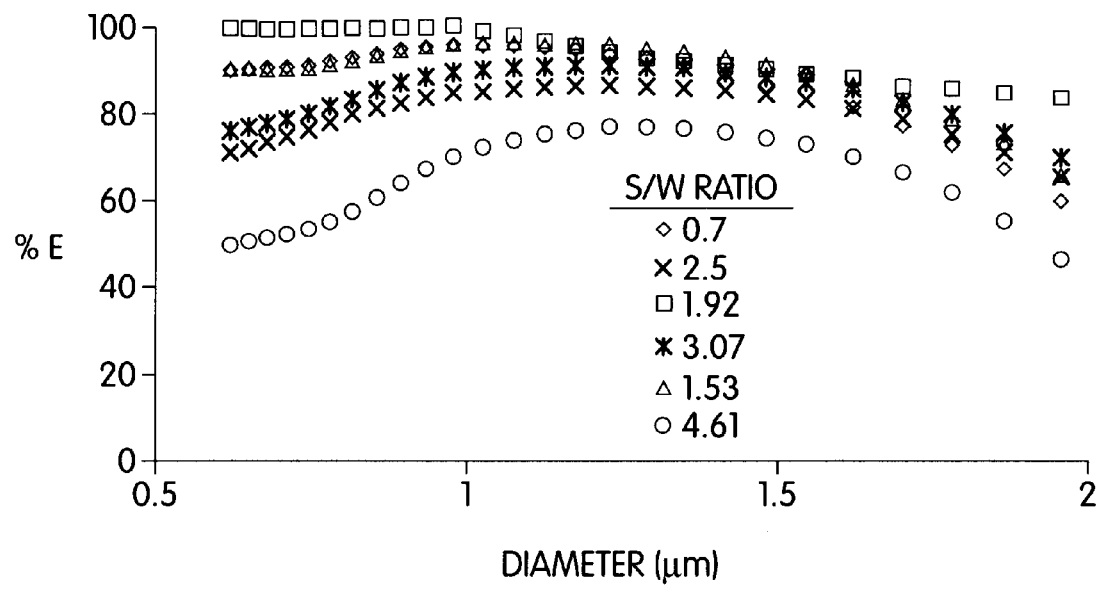
Figure 6D:
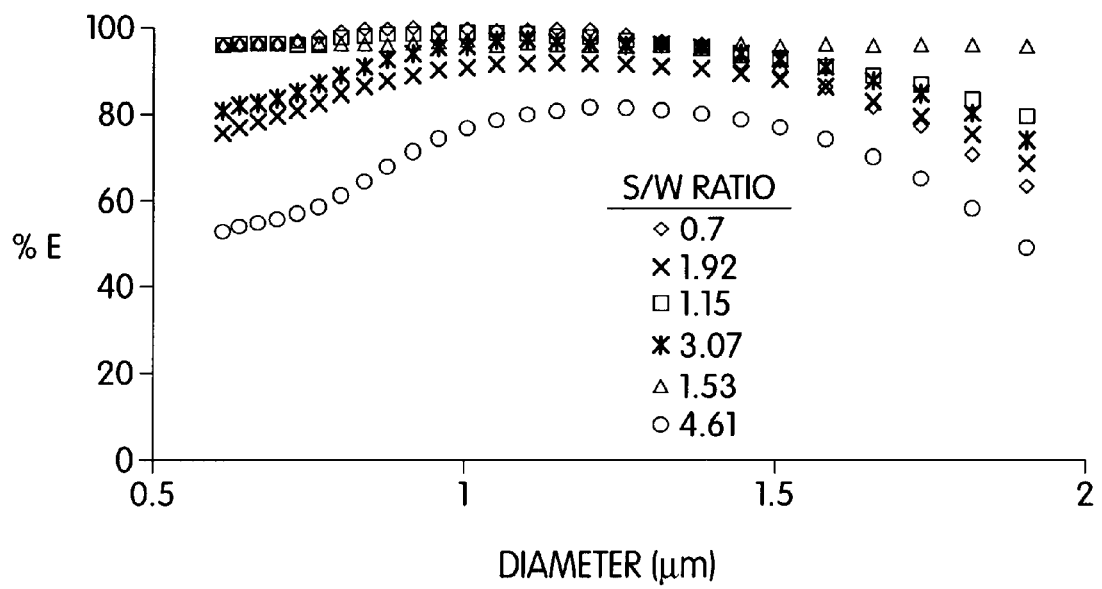
Figure 7:
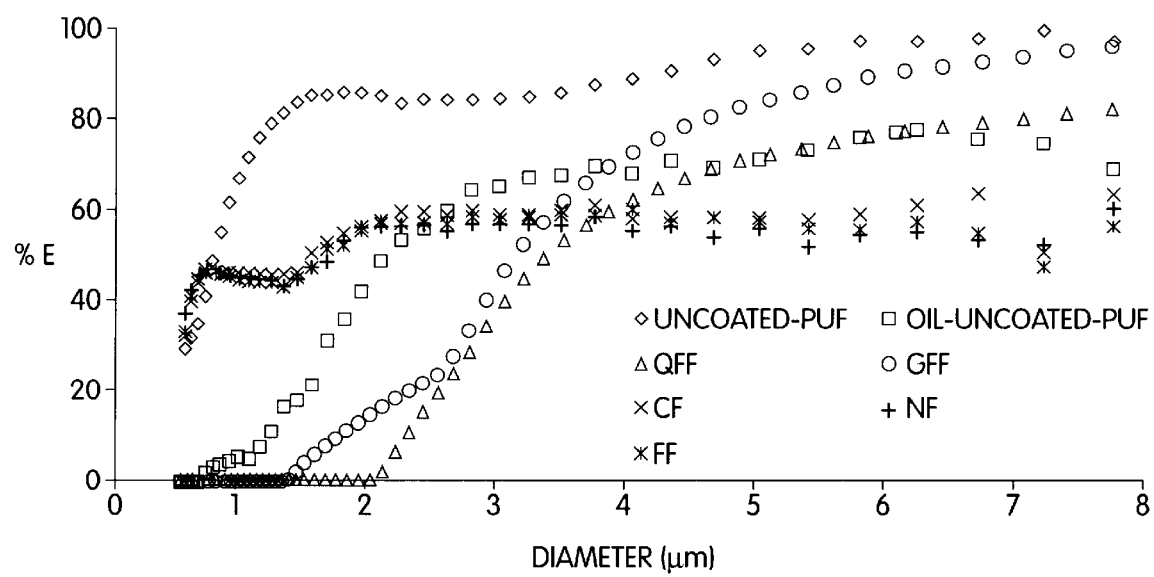
Figure 10:
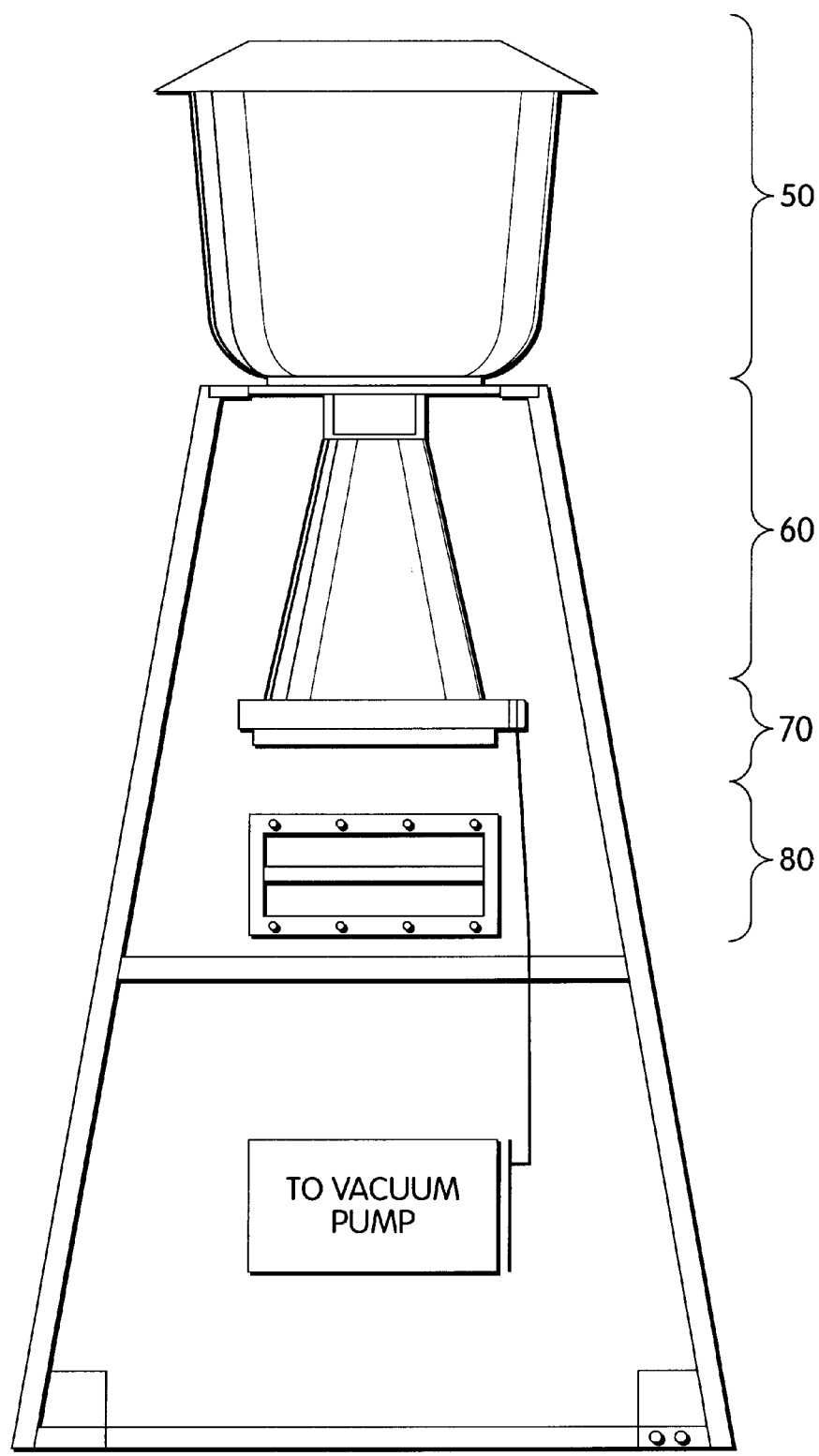

The high-volume low cut-off point impactor (HVLI) is depicted in FIG. 10. It consists of a 2.5 $\mu$m cut-point size-selective inlet 50 connected through a transition section 60 to a slit-nozzle conventional inertial impactor, operating at a flow of 1100 L/min, and comprising an acceleration nozzle 70 and an impaction substrate 80. The one-stage impactor uses polyurethane foam as the collection substrate and is shown schematically in FIG. 1. Two closely spaced slit-shaped acceleration jets (13.97[L]×0.03[W]cm) were used, with a theoretical 50% cut-off point of 0.16 $\mu$m at a flow rate of 550 L/min each ($\sqrt{Stk}$=0.50; Re=8736) (Hinds W. C., 1982). Particles with sizes below the impactor cut-off point can be collected on a filter, which can be installed downstream of the impactor. The collection substrate, located directly below the acceleration jet, was a piece of polyurethane foam (Merryweather Foam, Barbarton, Ohio; density: 0.019 g/cm$^3$) with dimensions of 32.00[L] by 0.63[W] by 0.63[H]cm. The distance between the acceleration nozzle and the impaction substrate was 0.08 cm, corresponding to a S/W ratio of 2.6 (ratio of the jet-to-surface distance, S, to the nozzle width, W). A Roots rotary lobe blower (Universal Rai Blower, Pelham, Ala.) powered by a 5 HP electrical motor was used. This vacuum pump was operating at 1750 r/min at 10.5 inches of Hg to obtain a flow rate of 1100 L/min through the inertial impactor.

HVLI Validation Tests

The objectives of these validation experiments were to: (i) determine the size cut-off point and losses of the impactor and (ii) investigate the properties of the polyurethane foam as impaction substrate. In order to perform these tests over the entire size range of fine and coarse particles (<10 $\mu$m), two different measuring instruments were used to measure the number concentration and size distribution of particles upstream and downstream of the impactor system. For particle sizes between 0.02 to 0.5 $\mu$m, the Scanning Mobility Particle Sizer (SMPS) (Model 3071A, TSI Inc., St. Paul, Minn.) equipped with a Condensation Particle Counter (CPC) (Model 3010, TSI Inc., St. Paul, Minn.) was used. For 0.5 to 10 $\mu$m, the Aerodynamic Particle Sizer (APS) (Model 3310A, TSI Inc., St. Paul, Minn.) was used. Ambient samples were collected using a prototype sampler and two Harvard Impactors (HI) in order to investigate the collection efficiency of HVLI under real conditions. Finally, the organic background of PUFs has been identified using gas chromatography/mass spectrometry techniques (GC-MS).

Methodology for Particle Measurements at Low Pressure

Both the SMPS and the APS required measurements of sample air at levels close to atmospheric pressure; however, in order to achieve the small size cut-off of about 0.10 $\mu$m, the pressure drop across the slit-nozzle acceleration jet was 0.25 atm. Thus, under normal operating conditions, it would be impossible to make measurements downstream of the impactor system with these instruments. A simple technique was employed in order to overcome this problem using a low flow vacuum pump which draws air from an isokinetic probe attached downstream of the sampler. The output flow of the vacuum pump was at atmospheric pressure. There was a concern about the effect that particles generated by the pump or lost within the pump had on number concentration and size distribution of laboratory-generated particles. The vacuum pump that was used was a linear-motor-driven free piston pump (Model VP, MEDO Inc., Hanover Park, Ill.). The operating principle of this pump minimized the generation of particles. An electromagnet drove the piston into and out of a cylinder, drawing air in through a one-way inlet spring valve and pushing it out through a similar valve. Because the pump flow can be adjusted by varying the power voltage, no additional valve (that could cause additional particle losses) was needed to control the flow rate (8.0 L/min). The flow rate of the MEDO pump as a function of the voltage was measured using calibrated flowmeters.

Figure 11:
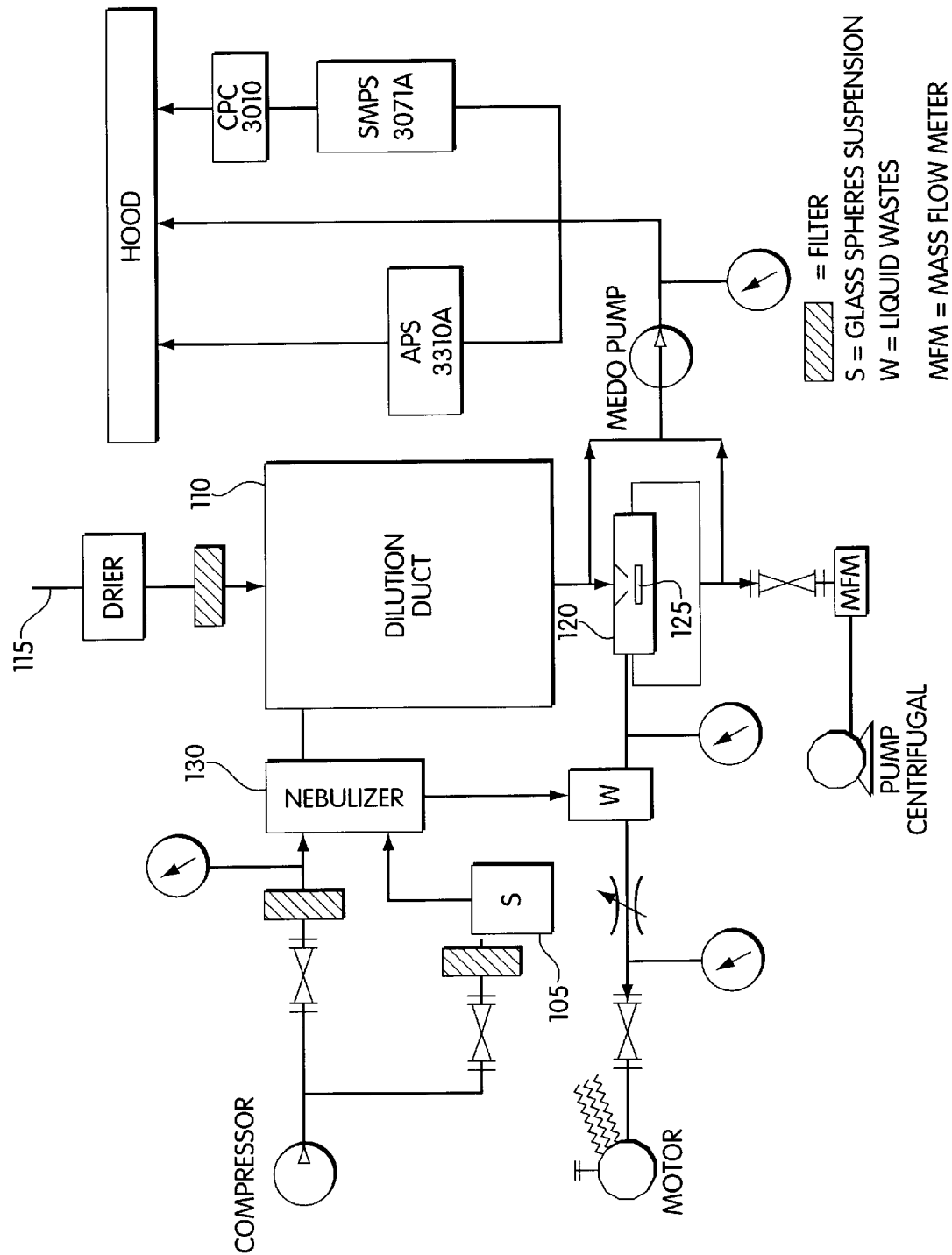
FIG. 11 depicts an inertial impactor used in experiments described herein.
Figure 12:
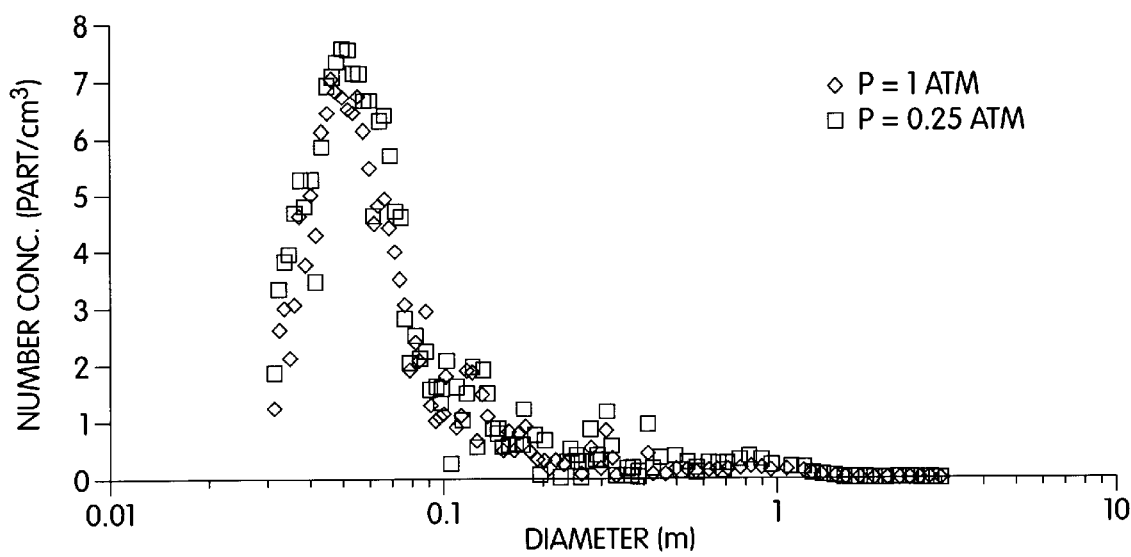
FIG. 12 illustrates the size distribution of particles generated under atmospheric pressure and under vacuum.

To determine the artifact particles produced by the MEDO pump as a function of particle size, a high efficiency particle air (HEPA) filter was attached to the inlet of the pump, and measurements were made at the outlet using both the SMPS and the APS instruments. Since the HEPA filter completely removed all particles from room air, particles measured at the pump outlet were generated by the pump. To determine the particle losses within the pump, test air containing polydisperse particles at atmospheric pressure was measured both with and without the MEDO pump in-line. Polydisperse particles were generated by nebulizing an aqueous suspension of 2–20 $\mu$m hollow glass spheres (density: 1.1 g/cm$^3$) (Polysciences, Inc, Warrington, Pa.) with a Retek Model X-70/N nebulizer, using filtered air at 7 psi. The aerosol was mixed with filtered room air to obtain test air.
Measurements Upstream and Downstream of the Impactor System The experimental setup is shown in FIG. 11. The test air mixture of polydisperse glass spheres 105 was passed into the top end of a vertical cylindrical duct 110 (100 cm[L]× 15.24 cm[ID]) made of anodized aluminum. Additional filtered room air was also added at the top of the duct 115. Turbulence was induced near the top of the duct, using a rectangular plate, to assure uniform concentration downstream. The sampler 120 was connected to the bottom of the duct 110. Alternate measurements were performed between an isokinetic probe in the duct, just upstream from the impactor system, and with a similar probe downstream of the impactor system. In each experiment, the concentration and size distribution of particles was measured for 10 minutes upstream, 10 minutes downstream, and then 10 minutes again upstream. This series of three tests was repeated twice for each experiment. Experiments were conducted on three different days, so that collection efficiency and losses were measured a total of nine times. To measure losses of particles as a function of size, for components of the impactor system, measurements at the inlet and outlet of the slit impactor system were conducted without the impaction substrate 125 in place.
Cleaning and Analysis of PUF The chemical background of the collection substrate is an important parameter in studying the organic aerosol, with this sampler and PUF as collection media. For this reason, pieces of polyurethane foam used in our experiments were sonicated with a series of organic solvents: methanol, ethyl acetate, hexane and methylene chloride for 1 hour. Furthermore, PUF pieces were ultrasonically extracted with 100 ml methylene chloride for 1 hour. The organic extract was concentrated and an aliquot of diazomethane was added for alcohols and acids derivatization. Finally, the extract was analyzed using gas chromatography (HP 5890)/mass spectrometry (HP 5971) in electron and chemical ionization for n-alkanes, polycyclic aromatic hydrocarbons (PAH), alcohols, acids, polychlorinated biphenyls (PCB), phenols and other functional organic compounds.
Characterization of the Low Flow Vacuum Pump Artifact particle concentrations generated by the low flow MEDO vacuum pump were found to be low and reproducible. The total particle number concentration for sizes 0.2 to 2.5 $\mu$m was 162±24 particles/cm$^3$ when pump was operating at atmospheric pressure and somewhat higher (185±19 particles/cm$^3$) under vacuum (0.25 atm). The number concentration of measured polydisperse particles both upstream and downstream of the impactor system (3775 and 1782 particles/cm$^3$, respectively) were ten to thirty times higher than the concentration of pump-generated particles; thus, the contribution of pump-generated particles was minor. The number distribution of pump-generated particles, as a function of particle diameter under atmospheric pressure (1 atm) and vacuum (0.25 atm) for nine different experiments is shown in FIG. 12. The number concentration increased rapidly from 0.02 to 0.04 $\mu$m, where it reached a maximum. For larger particle sizes the concentration decreased, with a concentration of 2.0 particles/cm$^3$ at about 0.1 $\mu$m; thus, a small number of particles between 0.1 and 2.5 $\mu$m was generated.

Substantial losses of particles were found to occur within the low flow MEDO pump. However, these losses were relatively stable as a function of the particle size. FIGS. 13A, 13B and 13C present number concentration (particles/cm$^3$) results for the mean of three different tests, measuring upstream (directly from the duct) and downstream (measuring after passing through the MEDO pump) for size ranges 0.2 to 0.7 $\mu$m and 0.7 to 2.5 $\mu$m, respectively (A,B), and the relative loss, as a percentage of the upstream concentration as a function of particle size (C). Tests were conducted using aerosolized hollow glass sphere aerosols, using the SMPS, and the APS. Losses of particles from 0.02 to 0.2 $\mu$m varied from 50 to 60% (C) but their size distribution did not change significantly (A,B). For sizes from 0.2 to 2.5 $\mu$m, losses were higher and varied from 60 to 75% (C). This could be explained by the higher inertial losses of larger particles.

Since the artifact particles generated by the MEDO pump were small and reproducible, and since the relative losses of particles, as a function of particle size were stable, and the distortion of size distribution was insignificant, it was possible to make adequate corrections to the number and size distributions of particles sampled both at the inlet and the outlet of the inertial impactor using this low flow vacuum pump.
Particle Losses in the Impactor Housing By comparing measurements at the inlet and outlet of the slit impactor system, the collection efficiency of the impaction substrate was determined. Particle losses were calculated by measuring the particle penetration through the sampler from which impaction substrate was removed. The observed losses (with the impaction substrate but without the substrate in place) were determined by comparing the measurements before the sampler (in the duct) and after the sampler (in the outlet connection of the sampler).

FIG. 14 shows the percent losses as a function of particle size. Losses for particles smaller than 1.0 $\mu$m were negligible; for sizes between 1.0 and 2.5 $\mu$m, losses were approximately 10%. It was previously observed that losses through the acceleration nozzle were negligible (Sioutas C., Ferguson S. T., Wolfson J. M., Ozkaynak H., Koutrakis P. (1997) *J. Aeros.Sci.*, 28, 1015–1028), and it was expected that there would be significant losses in the outlet manifold because of the highly turbulent flow in this area of the system. Since particles larger than the impactor's cut-off point were collected on the polyurethane foam, these losses do not affect the concentrations of particles collected onto a backup filter downstream of the impactor; however, measurements of losses were used to correct the sampler output aerosol concentrations in order to accurately calculate the substrate collection efficiency and the 50% cut-off point.

PUF Substrate Collection Efficiency

The type of polyurethane foam (density 0.019 g/cm$^3$; Merryweather Foam, Barberton, Ohio) was selected because of its low blank levels of elemental and organic pollutants. Also, preliminary tests have shown negligible interferences for biological and toxicological studies (Salonen, R. O., Pennanen, A. S., Halinen, A. I., Hirvonen, M-R., Silanpss, M., Hillamo R., Koskentalo, T., Aarnio, P., Ferguson, S. T. and Koutrakis, P. (1999) A chemical and toxicological comparison of urban air PM$_{10}$, collected during winter and spring in Finland, Paper presented at 3$^{rd}$ Colloquium on Particulate Air Pollution and Human Health, Jun. 6–8, 1999, Durham, N.C., USA). Finally, this type of polyurethane foam has anti-static properties, which will inhibit the build-up of electrostatic charge during sample collection and storage. FIG. 15 shows the collection efficiency curve for the slit-nozzle system with the PUF impaction substrate. To determine the 50% cut-off diameter and the slope of the collection efficiency curve, the experimental data were fitted using the Marquardt-Levensberg sigmoidal least-squares curve-fitting algorithm (Origin, Microcal Software Inc.). The correlation coefficient ($R^2$) was 0.99. The experimental 50% cut-off point ($d_{50}$) was 0.12 $\mu$m ($\sqrt{Stk}$=0.40) which was slightly lower than the theoretical value (0.16 $\mu$m).

This difference indicated that smaller particles could impact onto the collection medium and penetrate within the PUF. This mechanism eliminated bounce-off and re-entrainment artifacts; thus, the characteristics of the impactor remained stable for longer sampling periods. The standard geometrical deviation ($\sigma_g$) was 1.28, indicating a favorable separation of particles below and above the cut-off point. As mentioned above, the calibration experiment (which included three 10-minutes runs for each setup) was repeated nine times in total. In addition, the evaluation of losses within the MEDO pump was performed during each experiment and thus the collection efficiency curve was calculated separately for each experiment. The precision of both losses and calibration curve for each experiment was very high (less than 2%).

Field Validation Tests

Field tests were conducted to evaluate the performance of the impactor. A PM$_{0.12}$ slit-shaped impactor downstream of a PM$_{2.5}$ size selective inlet was used. An acceleration nozzle having dimensions of 5.84[L]×0.03[W]cm, which operated at the collection rate of 230 L/min, was used. The dimensions of PUF substrate were 6.60[L]×0.60[W]×0.30[H]cm. Different S/W ratios (2.31 and 3.08) were tested. Sampling was also performed using the Harvard Impactor (HI) (with oil-impregnated porous stainless steel substrate). This impactor has a size cut-off of 2.5 $\mu$m and operates at 10 L/min (Marple, V. A., Rubow, K. L., Turner, W. R. and Spengler, J. D. (1987) *Journal of Air Pollution Control Association* 37, 1303–1307). Particulate matter was collected on a Teflon filter.

Three samples were collected for 24, 48 and 72 hours. The PUF substrates were ultrasonically extracted with five (5) mL of ultra-pure H$_2$O for 90 minutes. Teflon filters were moistened with 50 $\mu$L of ethanol prior to being ultrasonically extracted with 5 mL of ultra-pure H$_2$O of for twenty minutes. The extractable material was analyzed for sulfate anion (SO$_4^{2-}$) by ion chromatography.

As shown in Table 3, better agreement was observed when the S/W ratio was 3.08. Bounce-off of fine particles could be the responsible for the low HVLI/HI ratio when the S/W ratio was 2.31. Sulfate concentrations measured by the Harvard Impactor (HI) were similar to those measured with HVLI at S/W ratio of 3.08. In addition, the values of the ratio HVLI/HI are close to unit (0.88–0.99), indicating that the HVLI can be used for collection by impaction of ambient particles.

TABLE 3

| | Sulfate Concentration ($\mu$gr/m$^3$) | | |
|---|---|---|---|
| S/W Ratio | Harvard Impactor (HI) | High Volume Low Cut-off Impactor (HVLI) | HVLI/HI Ratio |
| 2.31 | 5.36 | 3.52 | 0.66 |
| 3.08 | 2.98 | 2.56 | 0.86 |
| 3.08 | 1.57 | 1.38 | 0.88 |
| 3.08 | 2.98 | 2.96 | 0.99 |
| 3.08 | 2.98 | 2.86 | 0.96 |

Capacity Tests

Figure 16:
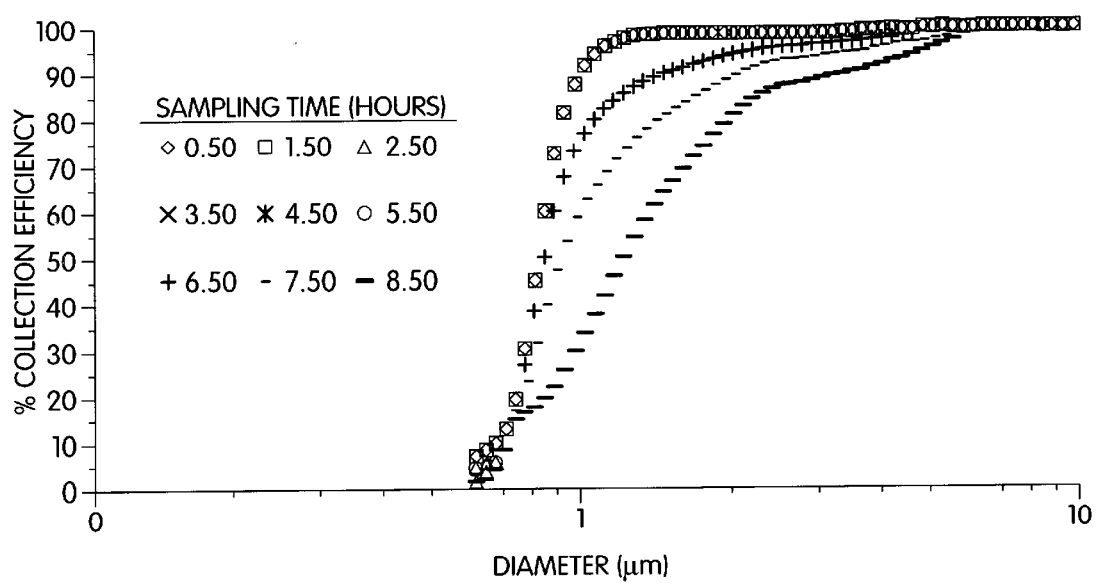

Laboratory tests were performed to examine the collection efficiency of particles as a function of the total amount of particles collected. A slit-shaped acceleration jet (0.38 [L]×0.03[W]cm) at a flow of 15 L/min was used. The dimensions of the PUF substrate were 1.00[L] and 0.60[W] and 0.60[H]cm. The results of these tests were used to determine the maximum loading (capacity), below which the high collection efficiency curve of the impactor remained unchanged (FIG. 16). The collection efficiency curve did not change for the first 5.50 hours (330 minutes). For longer periods, there are decreasing efficiencies for collection of particles between 1.5 to 2 $\mu$mm.

The mass concentration of generated particles was 5 mg/m$^3$, thus for a flow of 15 L/min, and a sampling period of 330 minutes, the total collected mass is 24.75 mg. Note that 24.75 mg is the capacity for an impactor using a flow of 15 L/min, with an accelerator slit length of 0.38 cm. For a much higher flow of 1100 L/min the estimated capacity of the corresponding substrate using a slit length of about 27.94 cm is 1.81 g. Therefore, for a high ambient PM$_{2.5}$ concentration of about 100 $\mu$g/m$^3$ the sampler can be used to collect ambient particles for a sampling period of more than a week.

Chemical Background of PUFs

Figure 17:
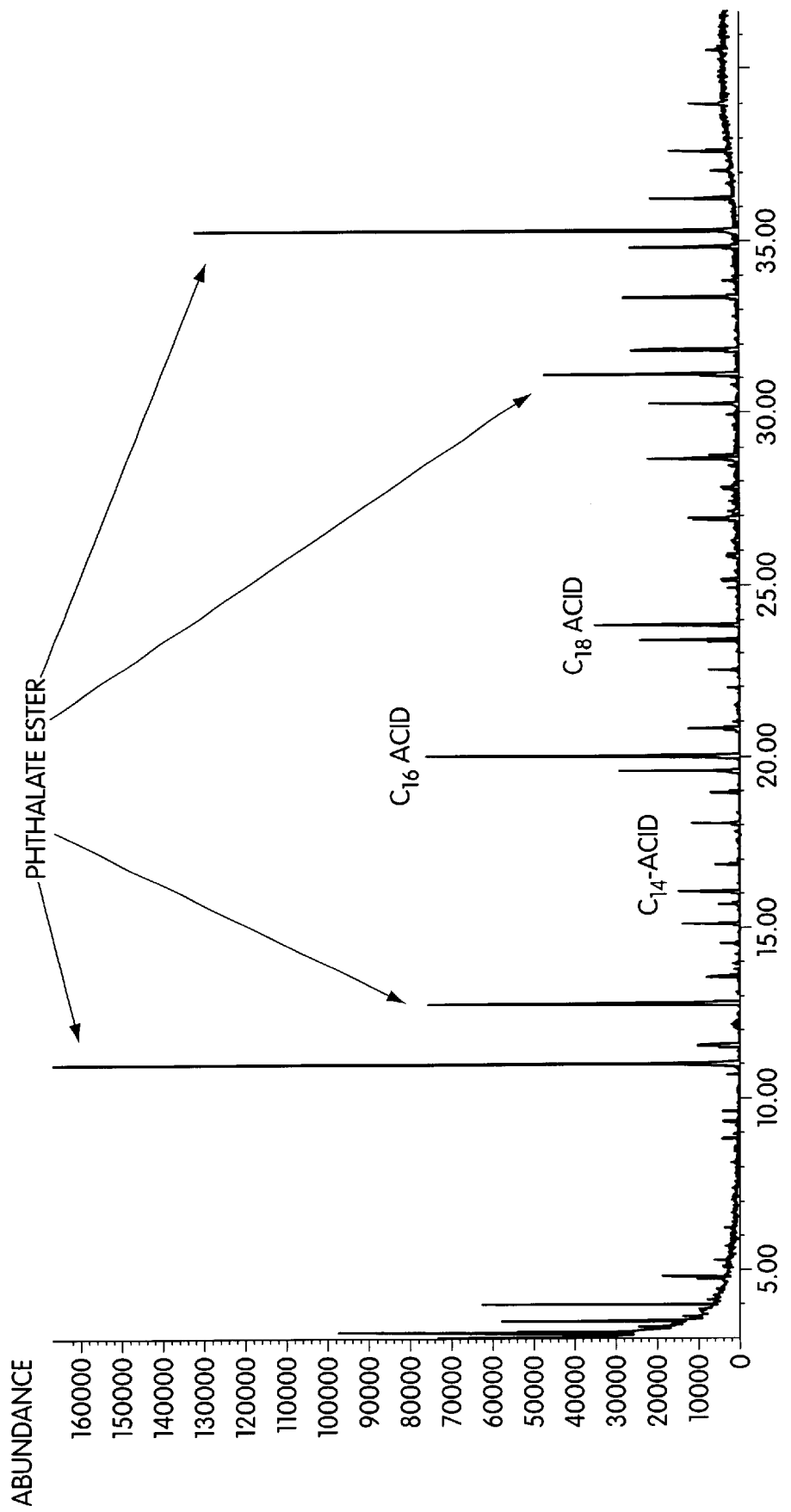

PUFs were pre-cleaned, extracted using ethyl acetate, methanol, n-hexane and dichloromethane, and analyzed using GC/MS to determine blank values for a number of organic compounds. A gas chromatogram of the organic extract is shown in FIG. 17. Polynuclear aromatic hydrocarbons and their oxygenated and nitrated products, and polychlorinated biphenyls were not identified in PUF extracts. In addition, phenols and other polar compounds were not detected. This suggests that PUF is suitable collection media for these compounds.

A series of phthalate esters (RT$_1$: 11.02 min; RT$_2$: 12.81 min; RT$_3$: 31.11 min; RT$_4$:35.31 min; m/z:149,165) and n-saturated acids (C$_{14}$ (RT: 16.61 min); C$_{15}$ (RT: 18.08 min); C$_{16}$ (RT: 20.03 min) and C$_{18}$ (RT: 24.03 min); m/z=74,87) were detected. The amounts of organic compounds detected in this organic extract were very low (~1 pg). If we assume an ambient concentration of C$_{15}$, which is lower than the other acids, of 10 ng/m$^3$, for a sampling period of 6 hours, the collected amount of C$_{15}$ will be 3.96 $\mu$g. This amount is two to three orders of magnitude higher than the amount of C$_{15}$ detected in the PUF. Thus, the use of PUF as an impaction substrate does not interfere the analysis of organic aerosol.

In addition, the effect of absorption of gaseous organics on the impaction substrate was expected to be unimportant because of the formation of a boundary layer above the impaction substrate. This boundary layer yielded slow mass transfer of gas phase species from the air sample to the PUF because the transfer phenomenon is governed by molecular diffusion. In addition, the impactor surface (PUF) was small and primarily covered by particles, thus the limiting active sites on which to collect organic gases.

A high volume inertial impactor has been developed. This impactor used a slit-shaped acceleration nozzle and an uncoated polyurethane foam as an impaction substrate/collection medium. As particles were collected, they penetrated within the polyurethane foam. This results in the minimization of particle losses due to bounce-off and re-entrainment.

A major feature of this sampler is that it can be used for a wide range of sampling durations, from a few hours to a week or more. Short sampling periods are feasible because the sampler has a high flow rate (1100 L/min). The ability to collect a relatively large amount of particles in a short period of time is important for studies which focus on time-resolved exposure and/or source apportionment studies. Long durations are feasible because of the high capacity of the collection substrate. Such long durations are sometimes required to achieve enough sensitivity for measurement of certain trace organics, and to collect sufficient quantities of particles for biological and toxicological analysis. One other important feature of this sampler is that polyurethane foam is chemically inert and non-toxic. Also, because particles are collected on a small impaction surface (20.16 cm$^2$), the extract volumes of solvent required for particle recovery are significantly smaller than for 20.32×25.4 cm filter based samplers. Overall, the development of this new instrument will make it possible to collect large amounts of particles for chemical analysis and toxicological studies. This will enable us to improve our knowledge of particle physicochemical properties and their health effects.

EXAMPLE 6

Polyurethane Foam Impactors

Figure 18:
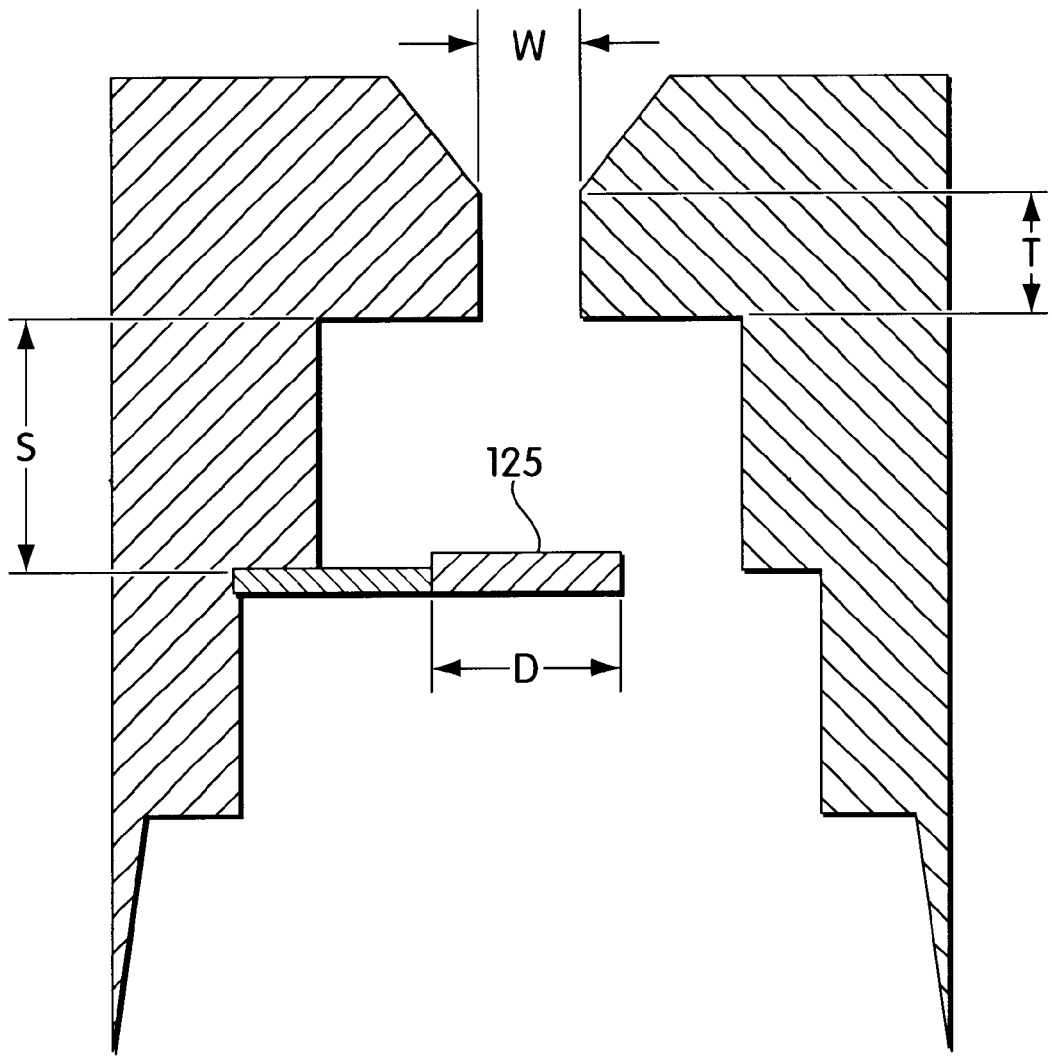
Figure 19:
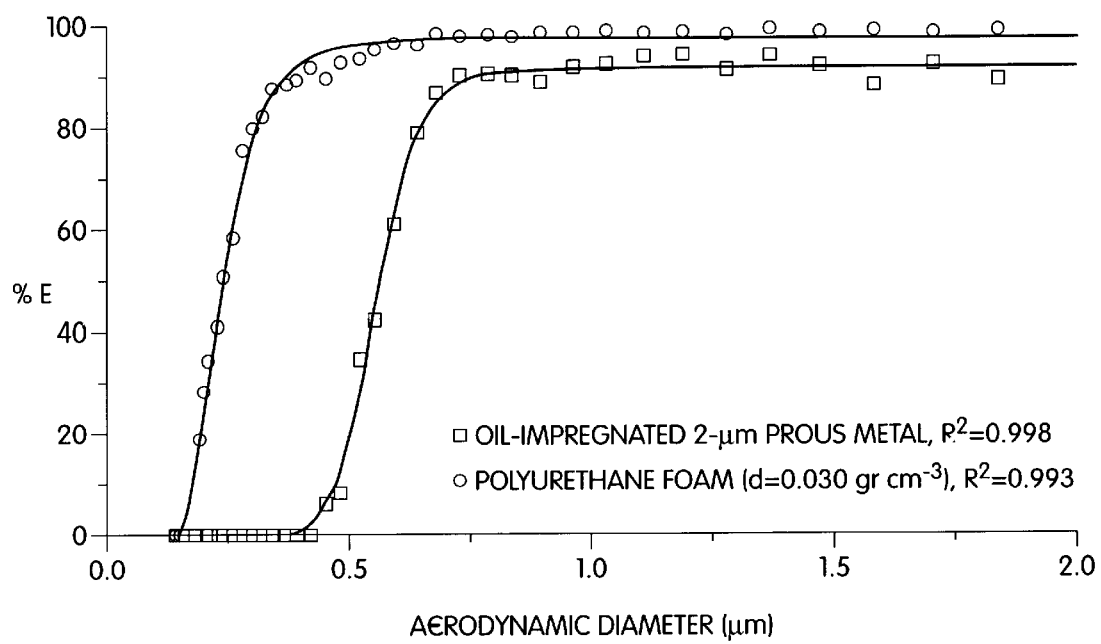
Figure 20A:
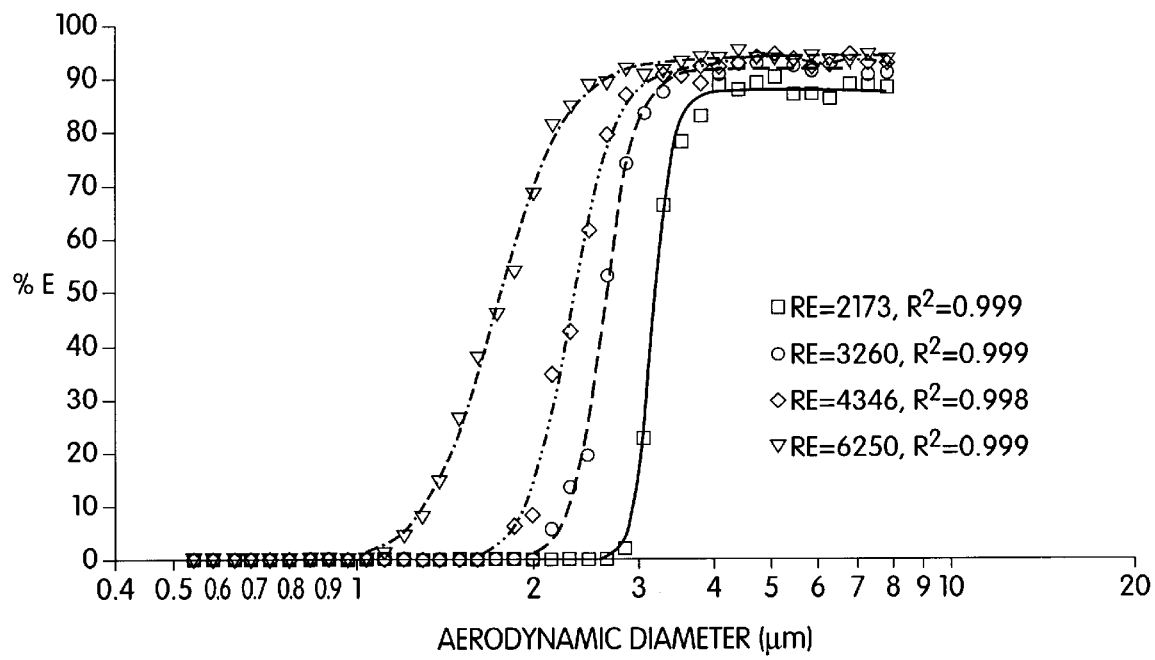
Figure 20B:
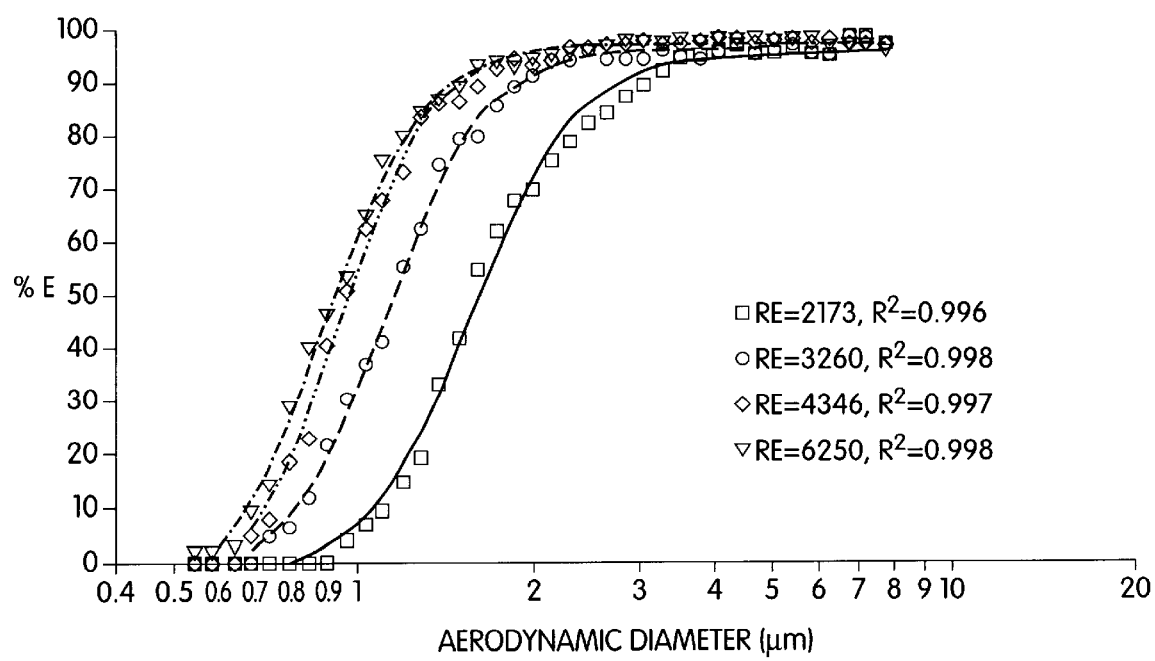
Figure 22:
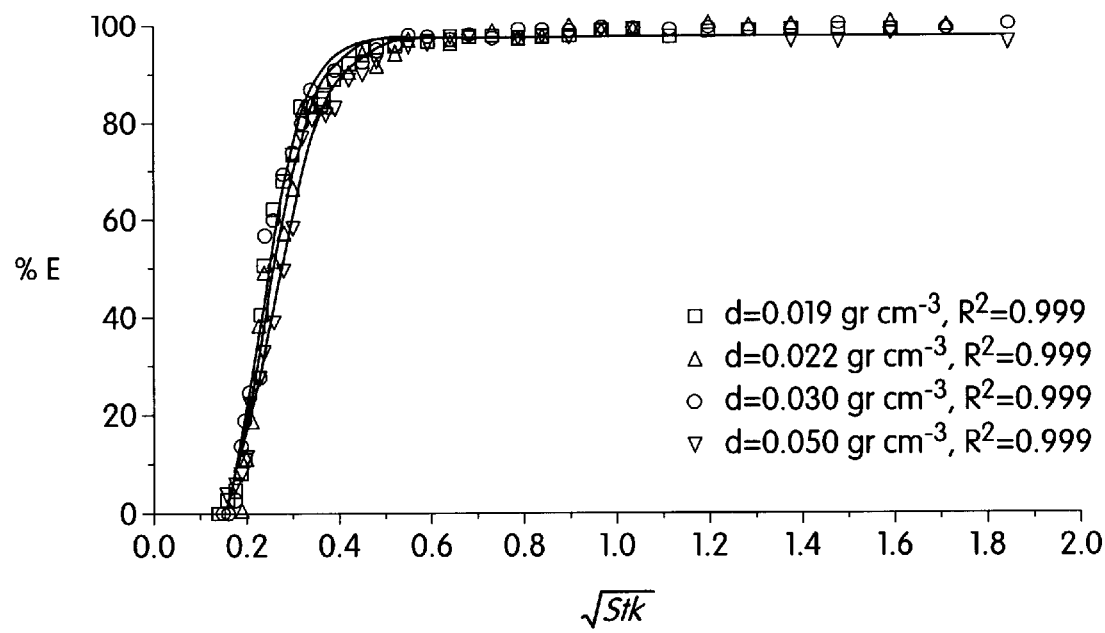
Figure 23:
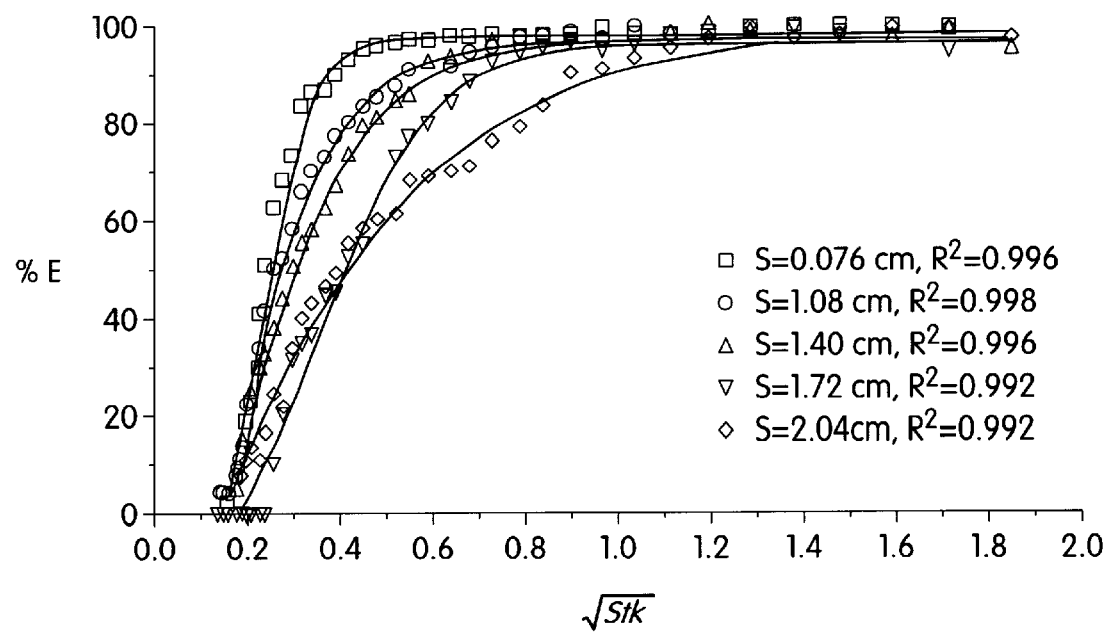

The Harvard Impactor (HI) sampler ($d_{50}$=2.43; Re=4414) (Air Diagnostics and Engineering, Inc., Harrison, Me.) (Marple, V. A., Rubow, K. L., Turner, W. R. and Spengler, J. D. (1987) *Journal of Air Pollution Control Association* 37, 1303–1307) was employed to investigate the feasibility of using polyurethane foam as an impaction substrate (FIG. 18). The jet diameter (W) is 0.32 cm at 10 L/min. The throat length (T) for the HI, T=0.46 cm, with T/W=1.43. The impaction substrate is an oil-coated porous metal disk impaction substrate with diameter of 2.54 cm. It is placed 0.76 cm below the nozzle of the impactor. Thus with this sampler, particles make two turns of 90° before they are collected on a filter.

The collection efficiency of PM$_{2.5}$ HI sampler was measured using both its standard impaction plate and PUF substrate. The collection efficiency of PUF at different nozzle-to-plate distances (S) and Reynolds numbers (Re) was also determined. The standard impaction substrate was replaced with different density polyurethane foams (PUF$_1$: $d_1$=0.019 g/cm$^3$ (Merryweather Foam, Barbarton, Ohio); PUF$_2$: $d_2$=0.022 g/cm$^3$ (SKC, Eighty Four, Pa.); PUF$_3$: $d_3$=0.030 g/cm$^3$ (McMaster-Carr Co. New Brunswick, N.J.); PUF$_4$: $d_4$=0.050 g/cm$^3$ (McMaster-Carr Co. New Brunswick, N.J.)).

The effect of the impaction substrate size, D (diameter of the disk), was also determined using both the oiled porous plate and PUF$_3$, with D between 0.95 to 2.54 cm. In addition, experiments were conducted using PUF with diameter S (0.32, 0.64, 0.95 and 1.58 cm) centered inside a nonporous 2.54-cm impaction plate to study the effect of the diameter of the "active" impaction surface on the collection efficiency. Other tests with the HI sampler with PUF$_3$ were conducted by increasing the nozzle-to-plate distance (S) from 0.76 to 2.04 cm, which corresponded to S/W ratios from 2.34 to 6.37. In addition, the Reynolds number was varied between 2397 to 6250, by adjusting the flow rate (Q) through the acceleration nozzle, corresponding to flow rates from 5 to 15 L/min.

The experimental apparatus is illustrated in FIG. 11. An aerosol of polydisperse particles with a nominal size range of 2–20 μm (hollow glass spheres, density 1.1 g/cm$^3$, Polysciences, Inc, Warrington, Pa.) was generated with a nebulizer 130 (Retek Model X-70/N), using an external reservoir of an aqueous suspension of the glass spheres 105. The generated aerosol was mixed with (relatively dry) filtered room air, and passed into the top end of a vertical anodized aluminum cylindrical duct 110 (35.0 cm [L]×7.6 cm [ID]). Additional filtered dry room air 115 was also added at the top of the duct to increase the total flow (2–12 L/min). Turbulence was induced near the top of the duct, using a rectangular plate, to assure uniform concentration downstream.

The sampler 120 was connected to the bottom of the duct. The size distribution of generated particles was measured upstream and downstream of the impactor system with an isokinetic probes. In each experiment, the concentration and size distribution of particles was measured for 5 minutes upstream, 5 minutes downstream and then 5 minutes again upstream. Each experiment was repeated at least nine times in order to get reproducible and accurate measurements of the number and the size distribution of generated particles. The Aerodynamic Particle Sizer (APS) (Model 3320, TSI Inc., St. Paul, Minn.) was used to measure particle number concentrations for aerodynamic diameters between 0.5 and 10 μm.

The collection efficiency for a given particle size was calculated as follows:

$$\%E = \left(1 - \frac{N_{downstream}}{N_{upstream}}\right) \times 100$$

were $N_{downstream}$ and $N_{upstream}$ were the number concentrations for a given particle size before and after the sampler. To determine the $d_{50}$ size and the geometrical standard deviation ($\sigma_g$) of the collection curve, the experimental data were fitted using the Levenburg-Marquardt non-linear least squares curve fitting algorithm (Origin, Version 5.0, MicroCal Software Inc.). The following equations were used to fit the experimental data.

$$\%E = \frac{A-B}{1+\exp\left(\frac{x}{C}-D\right)} + B \quad \text{and} \quad \%E = \frac{A-B}{1+\left(\frac{x}{C}\right)^d} + B$$

where %E is the percent collection efficiency; x is the square root of Stokes number ($\sqrt{Stk}$) and; A, B, C, D and d were regression constants. A and B correspond to minimum ($E_{min}$) and maximum ($E_{max}$) collection efficiency, respectively and; C, D and d. are factors related to the sharpness of the curve. The square root of Stokes number was calculated as follows:

$$\sqrt{Stk} = d_p \cdot \sqrt{\frac{p_p \cdot U \cdot C_c}{9 \cdot \mu \cdot W}}$$

where $\mu$ is the dynamic viscosity of the air (1.81 $10^{-4}$ g/(cm s)), $d_p$ is the particle aerodynamic diameter ($\mu$m), $p_p$ is the particle density (1.00 gr/m$^3$), W is the nozzle diameter (cm); U is the jet velocity (cm/s) and $C_c$ is the Cunningham slip correction factor.

The $d_{50}$, $d_{16}$ and $d_{84}$ values (the aerodynamic diameter of particles having collection efficiency of 50, 16 and 84%, respectively) were calculated using the above equations. The square of the correlation coefficient ($R^2$) was higher than 0.99 for most tests. Sharpness (s) of the collection efficiency curve was estimated as follows (Hinds, W. C., 1999 *Aerosol Technology.* $2^{nd}$ Edition, New York, Wiley & Sons):

$$s = \sqrt{\frac{d_{84}}{d_{16}}}$$

Table 4 shows the design parameters and results for the following features: 1) nozzle diameter, W (cm); 2) nozzle-to-plate distance, S (cm); 3) diameter of impaction plate, D (cm); 4) type of impaction plate, 5) flow rate, Q (L/min); 6) Reynolds number, Re (dimensionless); air velocity, U (cm/sec); 7) theoretical $d_{50}$ ($\mu$m); 8) experimental $d_{50}$ ($\mu$m); 9) square root of the Stokes number, $\sqrt{Stk}$ (dimensionless); 10) geometric standard deviation, $\sigma_g$ (dimensionless); 11) maximum collection efficiency $E_{max}$ (%) and; 12) pressure drop, ΔP (atm).

The collection efficiency (%E) curves of HI with its standard impaction substrate and $PUF_3$ are shown in FIG. 19. The experimental $d_{50}$ value with standard impaction substrate was 2.48 $\mu$m. It was slightly higher than the theoretical value ($d_{50(HI)}$=2.43 $\mu$m; Table 4). The geometric standard deviation ($\sigma_g$) was 1.17. However, for the HI sampler, the collection of coarse particles ($d_p \geqq 3$ $\mu$m; $\sqrt{Stk} \geqq 0.8$) was not efficient ($E_{max}$=92.7%) which indicates that bounce-off losses occurred from the impaction substrate (using oil-coated porous metal) (FIG. 19).

The experimental $d_{50}$ values for HI with PUF substrate was 1.12 $\mu$m ($\sqrt{Stk}$=0.24) (Table 4). As shown in FIG. 19, the $d_{50}$ value was substantially lower than both the nominal (theoretical) and experimental $d_{50}$ for its standard impaction plate. The geometric standard deviation ($\sigma_g$) was 1.32 $\mu$m with PUF, which is higher than the corresponding values for standard impaction plates. This indicates that separation of particles below and above the $d_{50}$ for PUF is not quite as good as with the standard substrates. Another important observation was that a lower $d_{50}$ was achieved at a relatively low pressure drop (ΔP=1.9 $10^{-2}$ atm), with PUF substrates. This feature allows for less vaporization of semi-volatile components during sampling, especially for the classification and collection of ultrafine particles.

The smaller cut-off size for PUF compared to standard substrates may be explained by a variety of possible mechanisms. The relatively large open pore space within the PUF impaction substrate could result in the formation of a boundary layer below the nominal surface, yielding a different air flow pattern above the substrate compared with the solid surfaces of the standard substrates. For PUF, the air streamlines could be closer to the substrate, allowing particles with less inertia to cross streamlines and to be

TABLE 4

| | Design Parameters | | | | Impactor theoretical characteristics | | | | Impactor experimental characteristics | | | | |
|---|---|---|---|---|---|---|---|---|---|---|---|---|---|
| No. | W (cm) | S (cm) | D (cm) | Impaction Plate | Q (L/min) | U (cm/sec) | Re | Nominal $d_{50}$ ($\mu$m) | Experimental $d_{50}$ ($\mu$m) | $\sqrt{Stk}$ | $\sigma_g$ | $E_{max}$ | ΔP ($10^{-2}$ atm) |
| 1 | 0.32 | 0.76 | 2.54 | OIPM | 10.0 | 2072 | 4414 | 2.43 | 2.48 | 0.51 | 1.17 | 92.8 | 1.9 |
| 2 | 0.32 | 0.76 | 2.54 | $PUF_3$ | 10.0 | 2072 | 4414 | 2.43 | 1.12 | 0.25 | 1.32 | 97.6 | 1.9 |
| 3 | 0.32 | 0.76 | 2.54 | OIPM | 5.0 | 1036 | 2207 | 3.47 | 3.36 | 0.48 | 1.09 | 87.3 | 0.6 |
| 4 | 0.32 | 0.76 | 2.54 | OIPM | 7.5 | 1554 | 3311 | 2.82 | 2.79 | 0.49 | 1.13 | 91.4 | 1.3 |
| 5 | 0.32 | 0.76 | 2.54 | OIPM | 10.0 | 2072 | 4414 | 2.43 | 2.48 | 0.51 | 1.17 | 92.7 | 1.9 |
| 6 | 0.32 | 0.76 | 2.54 | OIPM | 15.0 | 3108 | 6622 | 1.97 | 1.89 | 0.48 | 1.28 | 93.7 | 3.2 |
| 7 | 0.32 | 0.76 | 2.54 | $PUF_3$ | 5.0 | 1036 | 2207 | 3.47 | 1.76 | 0.25 | 1.42 | 95.6 | 0.6 |
| 8 | 0.32 | 0.76 | 2.54 | $PUF_3$ | 7.5 | 1554 | 3311 | 2.82 | 1.30 | 0.24 | 1.37 | 96.4 | 1.3 |
| 9 | 0.32 | 0.76 | 2.54 | $PUF_3$ | 10.0 | 2072 | 4414 | 2.43 | 1.12 | 0.24 | 1.32 | 97.1 | 1.9 |
| 10 | 0.32 | 0.76 | 2.54 | $PUF_3$ | 15.0 | 3108 | 6622 | 1.97 | 1.07 | 0.28 | 1.34 | 97.5 | 3.2 |
| 11 | 0.32 | 0.76 | 2.54 | $PUF_1$ | 10.0 | 2072 | 4414 | 2.43 | 1.13 | 0.24 | 1.27 | 97.6 | 1.9 |
| 12 | 0.32 | 0.76 | 2.54 | $PUF_2$ | 10.0 | 2072 | 4414 | 2.43 | 1.12 | 0.24 | 1.32 | 97.4 | 1.9 |
| 13 | 0.32 | 0.76 | 2.54 | $PUF_3$ | 10.0 | 2072 | 4414 | 2.43 | 1.12 | 0.24 | 1.31 | 98.3 | 1.9 |
| 14 | 0.32 | 0.76 | 2.54 | $PUF_4$ | 10.0 | 2072 | 4414 | 2.43 | 1.23 | 0.26 | 1.35 | 97.9 | 1.9 |
| 15 | 0.32 | 1.08 | 2.54 | $PUF_3$ | 10.0 | 2072 | 4414 | 2.43 | 1.12 | 0.24 | 1.32 | 97.6 | 1.9 |
| 16 | 0.32 | 1.40 | 2.54 | $PUF_3$ | 10.0 | 2072 | 4414 | 2.43 | 1.22 | 0.26 | 1.54 | 98.1 | 1.9 |
| 17 | 0.32 | 1.72 | 2.54 | $PUF_3$ | 10.0 | 2072 | 4414 | 2.43 | 1.36 | 0.29 | 1.61 | 98.5 | 1.9 |
| 18 | 0.32 | 2.04 | 2.54 | $PUF_3$ | 10.0 | 2072 | 4414 | 2.43 | 1.78 | 0.37 | 1.52 | 98.0 | 1.9 |
| 19 | 0.32 | 2.36 | 2.54 | $PUF_3$ | 10.0 | 2072 | 4414 | 2.43 | 1.82 | 0.38 | 1.93 | 103.2 | 1.9 |
| 20 | 0.32 | 0.76 | 2.54 | OIPM | 10.0 | 2072 | 4414 | 2.43 | 2.48 | 0.51 | 1.17 | 97.6 | 1.9 |
| 21 | 0.32 | 0.76 | 1.58 | OIPM | 10.0 | 2072 | 4414 | 2.43 | 2.52 | 0.52 | 1.22 | 89.9 | 1.9 |
| 22 | 0.32 | 0.76 | 0.95 | OIPM | 10.0 | 2072 | 4414 | 2.43 | 2.41 | 0.50 | 1.22 | 86.6 | 1.9 |
| 23 | 0.32 | 0.76 | 2.54 | $PUF_3$ | 10.0 | 2072 | 4414 | 2.43 | 1.12 | 0.24 | 1.32 | 97.6 | 1.9 |
| 24 | 0.32 | 0.76 | 1.58 | $PUF_3$ | 10.0 | 2072 | 4414 | 2.43 | 1.12 | 0.24 | 1.34 | 97.4 | 1.9 |
| 25 | 0.32 | 0.76 | 0.95 | $PUF_3$ | 10.0 | 2072 | 4414 | 2.43 | 1.12 | 0.24 | 1.46 | 93.5 | 1.9 |
| 26 | 0.32 | 0.76 | 1.58[1] | $PUF_3$ | 10.0 | 2072 | 4414 | 2.43 | 1.19 | 0.25 | 1.31 | 97.5 | 1.9 |
| 27 | 0.32 | 0.76 | 0.95[1] | $PUF_3$ | 10.0 | 2072 | 4414 | 2.43 | 1.33 | 0.28 | 1.28 | 95.1 | 1.9 |
| 28 | 0.32 | 0.76 | 0.64[1] | $PUF_3$ | 10.0 | 2072 | 4414 | 2.43 | 1.43 | 0.30 | 1.42 | 92.0 | 1.9 |
| 29 | 0.32 | 0.76 | 0.32[1] | $PUF_3$ | 10.0 | 2072 | 4414 | 2.43 | 1.70 | 0.35 | 1.41 | 95.3 | 1.9 |

[1]It is the PUF diameter which was centered in a 2.54 cm impaction plate; the rest was sealed with a non-porous material impacted and collected onto the substrate. The apparent reduction in particle bounce-off using PUF could be explained by a mechanism whereby a substantial fraction of the particles that may bounce off after impaction may be subsequently trapped on the internal walls of the open pores of the PUF. Another possible explanation is that the flexibility of the PUF pore walls allows for more absorption of excess particle kinetic energy than occurs with the more rigid standard substrates. The consequences of these possible mechanisms are that many layers of pre-collected particles could be formed, without significant deterioration of collection efficiency, with the potential for greater collection capacity than with conventional substrates. Indeed, experiments showed that the capacity of the substrate (impaction substrate surface: 0.84 cm$^2$; impaction substrate depth: 0.32 cm) is 1.81 g corresponding to 2.15 g/cm$^2$. This is more than two orders of magnitude higher than those observed for uncoated (0.43 mg/cm$^2$) and oil-coated (1.37 mg/cm$^2$) impaction substrates (Tsai, C. J. and Cheng, Y. H. (1995) *Aerosol Science and Technology* 23:96–106)

The following sections present the results of the subsequent collection efficiency tests based on varying the different design parameters, using the PUF substrates:

3.1 Effect of Reynolds Number (Re)

Figure 24A:
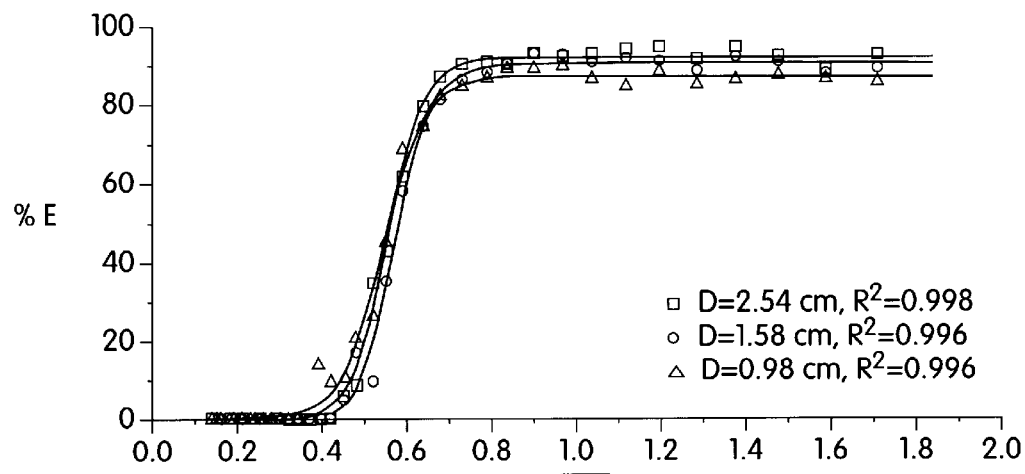
Figure 24B:
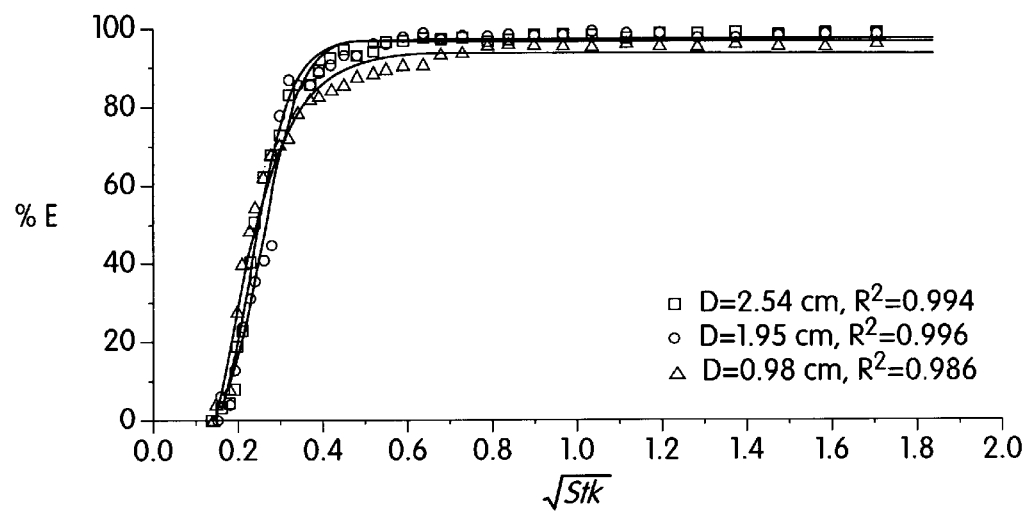
Figure 24C:
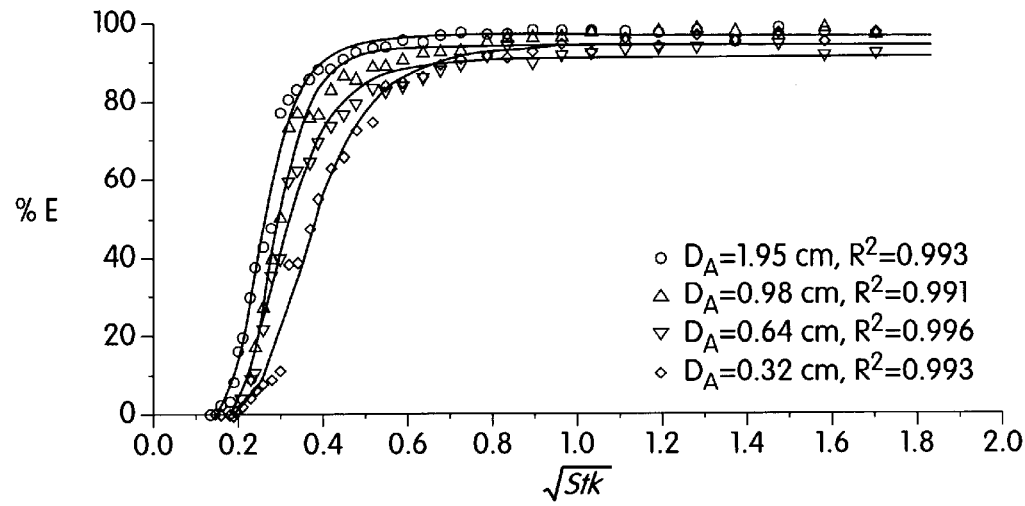

The magnitude of the air flow through the acceleration nozzle determines whether inertial or viscous forces dominate. This feature is mathematically expressed by the Reynolds number, Re (Hinds, W. C., 1999. *Aerosol Technology* $2^{nd}$ Edition, New York, Wiley & Sons). A value of Re higher than 1000 results in turbulent flow, with inertial forces dominating, while lower Re values indicate laminar flow, with viscous forces dominating. For a given nozzle, the Re value increases with increasing flow.

FIG. 20*a* shows the collection efficiency curves for the HI acceleration nozzle at four different flow rates (5, 7.5, 10, and 15 $L/min^1$, for $Q_1$, $Q_2$, $Q_3$, and $Q_4$, respectively) with corresponding Re values of 2207, 3311, 4414 and 6622), using oil-coated porous metal as the impaction substrate (diameter, D=2.54 cm). FIG. 20*b* shows the corresponding results for the same values of Q, using $PUF_3$ as the impaction substrate (D=2.54 cm). FIG. 21 shows the $d_{50}$ values for both substrates, as a function of Re.

For the oil-coated porous metal substrate, the $d_{50}$ decreased from 3.36 $\mu$m ($\sqrt{Stk}$=0.48, $Q_1$=5 L/min; Re=2207) to 1.89 $\mu$m ($\sqrt{Stk}$=0.48, $Q_4$=15 L/min; Re=6622) (Table 4). These $d_{50}$ values were slightly lower than the ones predicted by theory (for $\sqrt{Stk}$=0.50, the corresponding values of $d_{50}$ for $Q_1$, and $Q_4$, were 3.47, and 1.97 $\mu$m respectively). The geometric standard deviation, $\sigma_g$, increased with Re. The corresponding $\sigma_g$ values were 1.09 and 1.28, for Re values of 2207 and 6622, respectively. For the highest value of Re (6622) there was an enhanced collection efficiency of particles with size$\geqq d_{50}$. The maximum collection efficiency ($E_{max}$) also increased with increasing values of Re. For particle sizes$\geqq$3 $\mu$m, $E_{max}$ increased from 87.3 to 93.7% when Re changed from 2207 to 6622 (Table 4).

With $PUF_3$ as the substrate there was, in general, the same pattern as with the oiled porous metal, with the value of $d_{50}$ decreasing from 1.76 to 1.07 $\mu$m for Re values of 2207 and 6622, respectively. For all values of Re, the $d_{50}$ corresponded to $\sqrt{Stk}$=0.24±0.01. The theory for flat impaction substrates predicts values of $d_{50}$ corresponding to values of S=0.50, independent of Re value; however, the observed $d_{50}$ values for $PUF_3$ were substantially lower than the corresponding theoretical values (3.47 and 1.97 $\mu$m, for Re values of 2207 and 6622, respectively). As with the standard substrate, for $PUF_3$ the values of $\sigma_g$ slightly varied with flow rate, but they were higher than the corresponding values for the oiled metal substrate. Finally, the maximum collection efficiency values for $PUF_3$ were higher than the corresponding values for the standard substrate and increase with Re.

3.2 Effect of Polyurethane Foam Density

Many types of PUF are commercially available, and the effects on collection efficiency are likely to vary with different PUF properties. In this study, the effect of PUF density (ρ, in $g/cm^3$) on particle collection efficiency was investigated (FIG. 22). Particle collection efficiency did not change substantially for densities varying between 0.019 and 0.030 $g/cm^3$; however, there was a slight decrease in the collection efficiency for larger particle sizes when the highest density PUF was used (ρ=0.050 $g/cm^3$). The maximum collection efficiency remained stable and high ($E_{max}$= 97.9–98.3%), indicating that the collection of larger particles was very efficient and that bounce-off losses were minimal. While there was no difference in the $d_{50}$ (1.12 $\mu$m) for densities of 0.019, 0.022 and 0.030 $g/cm^3$, there were slight differences in the sharpness of the collection efficiency curve (($\sigma_g$=1.27 for ρ=0.019 $g/cm^3$ and $\sigma_g$=1.31 for both ρ=0.022 and 0.030 $g/cm^3$).

3.3 Effect of Nozzle-to Plate Distance (S)

FIG. 23 shows the collection efficiency curves for nozzle-to-plate distance (S) values of 0.76, 1.08, 1.40, 1.72 and 2.04 cm, for HI samplers with $PUF_3$ substrates. The flow pattern, the thickness of the boundary layer and the strength of inertial forces are all affected by the value of S. In particular, the air streamlines become more widely separated with increases in the nozzle-to-plate distance, with de-acceleration and thus a thicker boundary layer. These results suggest that $\sigma_g$ increase with S. $\sigma_g$ with values of 1.32 to 1.93 were observed for S values of 0.76 and 2.04 cm, respectively, while the corresponding values of $d_{50}$ were 1.12 and 1.82 $\mu$m. These results confirm that the nozzle-to-plate distance is a critical factor, especially in the case of PUF where the collection efficiency appears to be strongly affected by the flow pattern and the thickness of boundary layer.

3.4 Effect of Impaction Plate Diameter (D)

Earlier studies have paid little attention to the effect of impaction plate diameter (D) on the performance of inertial impactors using flat plate substrates. It has been assumed that a substrate with a diameter of two to four times the nozzle diameter was adequate for high collection efficiency of particles above the theoretical $d_{50}$ and that larger impaction plates would not improve the impactor performance. However, it was uncertain whether this assumption was valid for the PUF substrate. FIGS. 24*a,b* show the results for the HI sampler for varying D (from 0.95 to 2.54 cm), using both oil-coated porous metal and PUF substrates.

There were only small effects of plate diameter on the $d_{50}$ and $\sigma_g$ values for the oiled porous metal substrate, (FIG. 24*a*; Table 4). For values of D of 0.95 and 2.54 cm, the corresponding values of $d_{50}$ were 2.41 and 2.48 $\mu$m; the values of $\sigma_g$ were 1.17 $\mu$m and 1.22 $\mu$m, respectively. However, $E_{max}$ decreased significantly when the smaller plate diameter was used (97.7% and 86.6%, for D values of 2.54 and 0.95 cm, respectively).

Similar effects of varying the substrate diameter were observed with PUF3. The values of $\sigma_g$ increased slightly from 1.32 for the original 2.54 cm diameter to 1.34 and 1.46 for diameters of 1.58 and 0.95 cm, respectively (Table 4). $E_{max}$ decreased from 97.6% for D=2.54 to 93.5% for D=0.95. These differences indicate that the diameter of the impaction surface and therefore the size of boundary layer has a significant impact on the collection efficiency of particles larger than the $d_{50}$.

A 2.54-cm diameter impaction substrate containing a central disk of $PUF_3$ with smaller diameters, with the outer annulus sealed with non-porous material was tested (FIG. 24c). These results show that for the smaller PUF disks (within the 2.54-cm diameter plate), there were higher values of $d_{50}$ and $\sigma_g$ than for a 2.54 cm PUF diameter. Specifically, while for the full 2.54 cm PUF the $d_{50}$ was 1,12 μm and $\sigma_g$ was 1.32, for central disk diameters of 0.32, 0.64, 0.95 and 1.58 cm, the corresponding $d_{50}$ and ($\sigma_g$) values were 1.70(1.41), 1.43(1.42), 1.33(1.28) and 1.19(1.31) μm, respectively. These results suggest that the disturbance of the flow pattern and the boundary layer on the surface of impaction plate due to the presence of a non-porous material controlled the collection characteristics. In addition, these results indicate that the suggested impaction diameter of two or three times the nozzle diameter was insufficient for maximum particle collection efficiency.

In conclusion, inertial impactors with rigid impactor substrates present bounce-off and re-entrainment artifacts that can seriously distort the size distribution of collected ambient particles. These artifacts are due to the high-energy collision between the accelerated particles and impaction substrate or pre-collected particles. These distortions can apparently be reduced by replacing conventional impaction substrates, such as oil-coated filters and porous metal plates, with PUF.

For the same flow and Reynolds number, use of the PUF substrate resulted in a much smaller $d_{50}$ values than those obtained with conventional substrates, indicating that the use of PUF causes significant changes in the impaction process. It is likely that the high porosity volume affects the flow pattern above the impaction substrate, resulting in a thinner boundary layer, and thus allowing particles with less inertia to collide with the substrate. Particles with enough excess kinetic energy which either bounce or get re-entrained from conventional substrates may penetrate deeply enough into the pores of the PUF to considerably reduce these artifact effects. For this reason PUF substrates has a large collection capacity. Because a lower $d_{50}$ was achieved at a low pressure drop with PUF than for conventional substrates, it is possible to reduce artifact vaporization of semi-volatile components during sampling, especially for the classification and collection of ultrafine particles.

All articles, publications and patents cited in this application are hereby incorporated by reference, in their entirety.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of collecting particles in an accelerated gas sample, comprising:
   passing said gas sample through an inertial impactor; and
   impacting particles in said gas sample on a dry porous foam material.

2. The method of claim 1, wherein said foam comprises at least one of polyurethane, polyethylene, polypropylene and polyester.

3. The method of claim 1, wherein said porous material is at least 0.2 mm thick.

4. The method of claim 1, further comprising measuring the quantity or composition of particles impacted on said porous foam material.

5. The method of claim 1, further comprising analyzing the composition of the airstream that has passed through the inertial impactor.

6. The method of claim 1, further comprising passing said gas sample through a size-selective inlet prior to impacting particles.

7. The method of claim 1, further comprising passing said gas sample through an acceleration nozzle prior to impacting particles.

8. The method of claim 1, wherein the porous material is substantially free of oil.

9. A method for sampling particles of a particular size range in a gas sample, comprising:
   passing said gas sample through a size-selective inlet to remove particles above a predetermined upper size from said gas sample;
   passing said gas sample through an acceleration nozzle; and
   collecting particles which pass through said acceleration nozzle on a dry porous impaction substrate, wherein said impaction substrate comprises foam.

10. The method of claim 9, wherein said foam comprises at least one of polyurethane, polyethylene, polypropylene and polyester.

11. The method of claim 9, wherein said acceleration nozzle is round.

12. The method of claim 9, wherein said acceleration nozzle is slit-shaped.

13. The method of claim 9, wherein said impaction substrate is substantially free of oil.

14. The method of claim 9, wherein said impaction substrate is at least about 0.2 mm thick.

15. The method of claim 13, wherein said impaction substrate is at least about 0.2 mm thick.

16. An inertial impactor, comprising:
   a sample inlet for receiving a stream of gas;
   a housing coupled to said sample inlet;
   an acceleration nozzle mounted within said housing to increase the velocity of the stream of gas; and
   an impaction substrate comprising a dry porous foam material disposed adjacent to said acceleration nozzle to collect particles from said stream of gas.

17. A multistage gas sampling system comprising a plurality of impaction substrates configured such that a stream of air will pass sequentially over the impaction substrates, wherein at least one of said substrates comprises a dry porous material.

18. A method of manufacturing an inertial impactor, comprising:
   providing a housing;
   mounting within said housing an acceleration nozzle; and
   mounting adjacent to said acceleration nozzle an impaction substrate comprising a dry porous foam material.

19. The method of claim 18, wherein said foam material comprises at least one of polyurethane, polyethylene, polypropylene and polyester.

20. The method of claim 18, wherein said impaction substrate is substantially free of oil.

21. The method of claim 18, wherein said impaction substrate is at least about 0.2 mm thick.

22. The method of claim 19, wherein said impaction substrate is substantially free of oil and is at least about 0.2 mm thick.

23. The method of claim 1, wherein said foam comprises polyurethane having a density of approximately 0.005 g/cm3 to approximately 0.100 g/cm3.

24. The method of claim 1, wherein said foam comprises polyurethane having a density of approximately 0.010 g/cm3 to approximately 0.050 g/cm3.

25. The inertial impactor of claim 16, wherein said foam material comprises at least one of polyurethane, polyethylene, polypropylene and polyester.

26. The inertial impactor of claim 16, wherein said foam comprises polyurethane having a density of approximately 0.005 g/cm3 to approximately 0.100 g/cm3.

27. The inertial impactor of claim 16, wherein said foam comprises polyurethane having a density of approximately 0.010 g/cm3 to approximately 0.050 g/cm3.

28. The inertial impactor of claim 16, wherein said acceleration nozzle is round.

29. The inertial impactor of claim 16, wherein said acceleration nozzle is slit-shaped.

30. The inertial impactor of claim 16, wherein said impaction substrate is substantially free of oil.

31. The inertial impactor of claim 16, wherein said foam is at least about 0.2 mm thick.

32. The inertial impactor of claim 25, wherein said foam is at least about 0.2 mm thick.

33. The method of claim 18, wherein said foam comprises polyurethane having a density of approximately 0.005 g/cm3 to approximately 0.100 g/cm3.

34. The method of claim 18, wherein said foam comprises polyurethane having a density of approximately 0.010 g/cm3 to approximately 0.050 g/cm3.

35. An inertial impactor, comprising:

an air inlet for receiving a stream of gas;

a housing coupled to said inlet;

an acceleration nozzle mounted within said housing to increase the velocity of said stream of gas; and an impaction substrate comprising a dry porous cloth material aligned with said acceleration nozzle to collect particles from said stream of gas.

36. The inertial impactor of claim 35, further comprising a size-selective inlet mounted within said housing to remove particles greater than a predetermined size from said stream of gas.

37. The inertial impactor of claim 35, wherein said cloth material comprises felt cloth.

38. The inertial impactor of claim 37, wherein said felt cloth is comprised of polyester.

39. The inertial impactor of claim 38, wherein said felt cloth has a nominal pore diameter of approximately 100 $\mu$m.

40. The inertial impactor of claim 35, wherein said acceleration nozzle is round.

41. The inertial impactor of claim 35, wherein said acceleration nozzle is slit-shaped.

42. The inertial impactor of claim 35, wherein said impaction substrate is substantially free of oil.

43. The inertial impactor of claim 35, wherein said impaction substrate is at least about 0.2 mm thick.

44. The inertial impactor of claim 38, wherein said impaction substrate is at least about 0.2 mm thick.

45. A method of collecting particles in an accelerated gas stream, comprising:

passing said gas stream through an inertial impactor; and impacting particles in said gas stream on a dry porous cloth material.

46. The method of claim 45, wherein said cloth material comprises felt cloth.

47. The method of claim 45, wherein said felt cloth is comprised of polyester.

48. The method of claim 45, wherein said felt cloth has a nominal pore diameter of approximately 100 $\mu$m.

49. The method of claim 45, further comprising measuring the quantity or composition of particles deposited on said porous cloth material.

50. The method of claim 45, further comprising analyzing the composition of said gas stream that has passed through said inertial impactor.

51. The method of claim 45, wherein said porous cloth material is at least 0.2 mm thick.

52. The method of claim 45, further comprising passing said gas stream through a size-selective inlet prior to impacting particles.

53. The method of claim 45, further comprising passing said gas stream through an acceleration nozzle prior to impacting particles.

54. The method of claim 45, wherein said dry porous cloth material is substantially free of oil.

55. A method for sampling particles of a particular size range in a gas sample, comprising:

passing said gas sample through a size-selective inlet to remove particles above a predetermined upper size from said gas sample;

passing said gas sample through an acceleration nozzle; and collecting particles which pass through said acceleration nozzle on a dry porous impaction substrate, wherein said impaction substrate comprises cloth.

56. The method of claim 55, wherein said cloth comprises polyester.

57. The method of claim 55, wherein said cloth is substantially free of oil.

58. The method of claim 55, wherein said acceleration nozzle is round.

59. The method of claim 55, wherein said acceleration nozzle is slit-shaped.

60. The method of claim 55, wherein said impaction substrate is at least about 0.2 mm thick.

61. A method of manufacturing an inertial impactor, comprising:

providing a housing;

mounting within said housing an acceleration nozzle; and mounting adjacent to said acceleration nozzle an impaction substrate comprising a dry porous cloth material.

62. The method of claim 61, further comprising mounting within said housing a size-selective inlet for removing particles above a predetermined size.

63. The method of claim 61, wherein said cloth material comprises felt cloth.

64. The method of claim 63, wherein said felt cloth is comprised of polyester.

65. The method of claim 61, wherein said impaction substrate is substantially free of oil.

66. The method of claim 61, wherein said impaction substrate is at least about 0.2 mm thick.

* * * * *